(12) United States Patent
Raines et al.

(10) Patent No.: US 9,085,590 B2
(45) Date of Patent: Jul. 21, 2015

(54) PROTECTING GROUPS FOR BORONIC ACIDS

(71) Applicant: Wisconsin Alumni Research Foundation, Madison, WI (US)

(72) Inventors: Ronald T. Raines, Madison, WI (US); Brett VanVeller, Madison, WI (US); Matthew Aronoff, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/213,433

(22) Filed: Mar. 14, 2014

(65) Prior Publication Data
US 2014/0275601 A1 Sep. 18, 2014

Related U.S. Application Data

(60) Provisional application No. 61/784,941, filed on Mar. 14, 2013.

(51) Int. Cl.
*C07F 5/04* (2006.01)
*C07F 5/02* (2006.01)

(52) U.S. Cl.
CPC .. *C07F 5/025* (2013.01); *C07F 5/04* (2013.01)

(58) Field of Classification Search
CPC ...................................................... C07F 5/04
See application file for complete search history.

(56) References Cited

U.S. PATENT DOCUMENTS

| | | | |
|---|---|---|---|
| 3,213,136 | A | 10/1965 | Washburn et al. |
| 5,594,111 | A | 1/1997 | Stolowitz |
| 5,594,151 | A | 1/1997 | Stolowitz |
| 5,623,055 | A | 4/1997 | Stolowitz |
| 5,744,627 | A | 4/1998 | Stolowitz et al. |
| 5,777,148 | A | 7/1998 | Stolowitz et al. |
| 5,837,878 | A | 11/1998 | Stolowitz et al. |
| 6,075,126 | A | 6/2000 | Stolowitz et al. |
| 6,124,471 | A | 9/2000 | Stolowitz et al. |
| 6,156,884 | A | 12/2000 | Ahlem et al. |
| 6,462,179 | B1 | 10/2002 | Stolowitz et al. |
| 6,630,577 | B2 | 10/2003 | Stolowitz et al. |
| 8,013,203 | B2 | 9/2011 | Burke et al. |
| 8,318,983 | B2 | 11/2012 | Burke et al. |
| 8,338,601 | B2 | 12/2012 | Burke et al. |
| 2012/0059184 | A1 | 3/2012 | Burke et al. |
| 2013/0196433 | A1 | 8/2013 | Raines et al. |

OTHER PUBLICATIONS

Alder et al. (1968) "The remarkable basicity of 1,8-bis(dimethylamino)naphthalene," *Chem. Commun.* 723-724.
Capicciotti et al. (Apr. 1, 2011) "Synthesis of C-Linked Triazole-Containing AFGP Analogues and Their Ability to Inhibit Ice Recrystallization," *Bioconjugate Chem.* 22:605-616.
Dent III et al. (2002) "9-BBN: An amino acid protecting group for functionalization of amino acid side chains in organic solvents," *Org. Lett.* 4:1249-1251.
Ellis et al. (Feb. 2012) "Boronate-Mediated Biologic Delivery," *J. Am. Chem. Soc.* 134:3631-3634.
Gillis et al. (2007) "A Simple and Modular Strategy for Small Molecule Synthesis: Iterative Suzuki—Miyaura Coupling of B-Protected Haloboronic Acid Building Blocks," *J. Am. Chem. Soc.* 129:6716-6717.
Gillis et al. (2008) "Multistep Synthesis of Complex Boronic Acids from Simple MIDA Boronates," *J. Am. Chem. Soc.* 130:14084-14085.
Gillis et al. (2009) "Iterative Cross-Coupling with MIDA Boronates: towards a General Strategy for Small-Molecule Synthesis," *Aldrichimica Acta.* 42:17.
Knapp et al. (2009) "A General Solution for Unstable Boronic Acids: Slow-Release Cross-Coupling from Air-Stable MIDA Boronates," *J. Am. Chem. Soc.* 131:6961-63.
Mancilla et al. (1986) "New bicyclic organylboronic esters derived from iminodiacetic acids," *J. Organomet. Chem.* 307:1-6.
Miyaura (1995) "Palladium-Catalyzed Cross-Coupling Reactions of Organoboron Compounds," *Chem. Rev.*, 95:2457-2483.
Molander et al. (2007) "Organotrifluoroborates: Protected Boronic Acids That Expand the Versatility of the Suzuki Coupling Reaction," *Acc. Chem. Res.* 40:275-286.
Molander et al. (2011) "Organotrifluoroborates: Organoboron Reagents for the Twenty-First Century," In; *Boronic Acids.* Wiley-VCH Verlag GmbH & Co. pp. 507-550.
Noguchi et al. (2007) "Boron-Masking Strategy for the Selective Synthesis of Oligoarenes via Iterative Suzuki-Miyaura Coupling," *J. Am. Chem. Soc.* 129:758-759.

(Continued)

*Primary Examiner* — Samantha Shterengarts
(74) *Attorney, Agent, or Firm* — Lathrope & Gage LLP

(57) ABSTRACT

Di- and trivalent protecting groups for organoboronic acids including phenyl boronic acids, benzoxaboroles and benzoxaborins, which are prepared from precursor compounds of formula I:

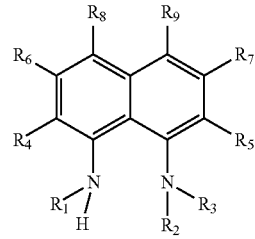

where: $R_1$ is a methyl, ethyl or a —$(CH_2)_n$—OH group, where n is 2 or 3; $R_2$ and $R_3$ are independently methyl or ethyl groups; $R_4$ and $R_5$ are independently halogens or hydrogens; $R_6$ and $R_7$ are independently hydrogens, halogens, or nitro groups; and $R_8$ and $R_9$ are independently hydrogens, halogens or nitro groups or $R_8$ and $R_9$ together with a portion of the naphthalene ring form a 5-member ring, where when $R_1$ is —$CH_2$—$CH_2$—OH then the protecting group is a trivalent protecting group. Also provided are protected organoboronic acids including protected phenyl boronic acids, benzoxaboroles and benzoxaborins. Also provides are methods for conducting reactions employing protected organoboronic acids.

30 Claims, No Drawings

(56) References Cited

OTHER PUBLICATIONS

Ozeryanskii et al. (2000) "Peri-naphthylenediamines 29. 1,8-bis(dimethylamino)-3-nitro- and -3,6-dinitronaphthalenes and 5,6-bis(dimethylamino)-3-nitro- and -3,8-dinitroacenaphthenes as the first representatives of "proton sponges" meta-substituted relative to $NMe_2$ groups," *Russian Chemical Bulletin*. (Translation of Izvestiya Akademii Nauk, Seriya Khimicheskaya) 49(8):1399-1405.

Ozeryanskii et al. (2005) "N,N,N'-Trialkyl-1,8-diaminonaphthalenes: convenient method of preparation from protonated proton sponges and the first X-ray information," *Tetrahedron*, 61(17):4221-4232.

Pal et al. (2010) "Design, synthesis, and screening of a library of peptidyl bis(boroxoles) as oligosaccharide receptors in water: identification of a receptor for the tumor marker TF-antigen disaccharide," *Angew. Chem., Int. Ed*. 49:1492-1495.

Van Veller et al. (Sep. 16, 2013) "A divalent protecting group for benzoxaboroles," *RSC Adv*. 3:21331.

Pozharskii et al. (1995) "1,8-Bis(dimethylamino)naphthalene. XIII. Solvatochromism and molecular structure of 4-nitro-1,8-bis(dimethylamino)naphthalene and its salt with perchloric acid," *Russian Journal of Organic Chemistry*. 31(4):525-535. (Translated from *Zhurnal Organicheskoi Khimii*. 31(4):570-81).

International Search Report with Written Opinion corresponding to International Patent Application No. PCT/US2014/028810, mailed Jul. 24, 2014.

PROTECTING GROUPS FOR BORONIC ACIDS

CROSS-REFERENCE TO RELATED APPLICATIONS

This application claims the benefit of U.S. provisional application 61/784,941 filed Mar. 14, 2013 which is incorporated by reference herein in its entirety.

STATEMENT REGARDING GOVERNMENT SUPPORT

This invention was made with government support under GM044783 awarded by the National Institutes of Health. The government has certain rights in the invention.

BACKGROUND OF THE INVENTION

The Lewis acidic properties of boronic acids, which derive from a vacant p-orbital, have been exploited for a variety of applications in reactions. Boronic acids are reported to have various biological and medicinal applications [Yang et al. 2005] and are of particular interest for saccharide chemosensing [James et al. 2005].
A variety of successful protecting group strategies have been developed to modulate undesired reactivity of boronic acids and allow for synthetic manipulation. A common example is the pinacol ester (illustrated in structure a below) which sterically shields the p-orbital from reaction. Similarly, Suginome and co-workers demonstrated the reduced reactivity of boronic acids when protected by 1,8-diaminonaphthalene (illustrated in structure b below) presumably due to electron delocalization of the nitrogen lone pairs onto the boron. [Noguchi et al. 2007; Noguchi et al. 2008] Another commonly employed strategy is based on the fluoro-affinity of boron to form trifluoroboronate salts (illustrated in structure c below) [Molander et al. 2011; Molander and Ellis 2007]. While highly stable, salts such as 5 are incompatible with chromatography, limiting their utility in multistep synthesis.

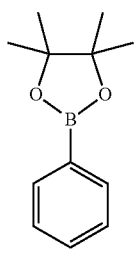

a

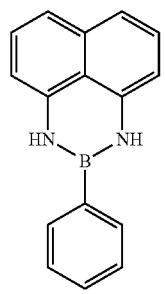

b

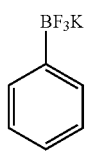

c

Burke and coworkers have popularized a three-coordinate N-methyliminodiacetic acid (MIDA) ligand for boronic acids that coordinates the vacant p-orbital with a trialkylamine to give a charge neutral adduct (6). [Gillis and Burke 2007; Gillis and Burke 2009; Knapp et al. 2009] The resulting complexes allow for broad compatibility with synthetic reagents and chromatographic purification. [Gillis and Burke 2008] U.S. Pat. Nos. 8,013,203, 8,318,983 and 8,338,601 relate to such three-coordinate iminodiacetic acid protecting groups and organoboronic acids protected by such protecting groups. The protected organoboronic acids are described as having a $sp^3$ hybridized boron and a conformationally rigid protecting group bonded to the boron.
The protected organoboronic acids are described in the patent by the formula:

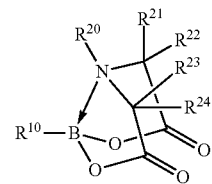

where $R^{10}$ is an organic group, $R^{20-24}$ are independently hydrogen or an organic group. MIDA is the species where $R^{20}$ is a methyl group and $R^{21-24}$ are all hydrogens.
Protecting groups for organoboronic acids are of particular interest for applications in Suzuki-Miyaura cross-coupling reactions [Miyaura and Suzuki 1995] between a boronic acid or ester and an organohalide or pseudo-halide. This coupling reaction is now widely used for the synthesis of complex organic molecules which involves the initial synthesis of chemically complex organoboronic acids or esters as reactants in the cross-coupling reaction. Because boronic acids react with many common reagents, synthesis of such complex organic boronic acid reactants is difficult and often requires introduction of the boronic acid group as the last step in the synthesis of the reactant.
Methods for introduction of the boronic acid group in addition may not be compatible with other common functional groups which enhances the complexity of syntheses of complex organoboronic reagents. The use of protecting groups for the boronic acid group which are tolerant to a wide range of reagents significantly reduces the complexity of synthesis of organoboronic acid reactants. Further, a protecting group must be removable by a method that does not detrimentally affect the functional groups on the organoboronic acid. In this regard, it is useful in the art to have various protecting groups which are removable by different means which may be more compatible for use with different organic functional groups.
Recent reports have emphasized the biological and therapeutic utility of oxaborole heterocyclic boronic acid variants called benzoxoboroles (also called benzoboroxoles). These variants have received increasing attention for applications in drug discovery, [Baker et al. 2009; Baker et al. 2011; Li et al.

2010; Rock et al. 2007; Obrecht et al. 2011; Qiao et al. 2012; Akama et al. 2009; Xia et al. 2011] synthetic methods, [Dixon et al. 2012] and biotechnology, [Ellis et al. 2012; Kim et al. 2012]. Benzoxaborole (1) [Adamczyk-Woźniaka 2009] in particular—characterized by a phenyl ring fused to a five-membered oxaborole—is perhaps the most widely employed oxaborole. The annulated benzylic alcohol in 1 appears to confer higher stability, [Snyder et al. 1958] lower $pK_a$ [Tomsho et al. 2012], and excellent sugar (diol) binding properties under physiological conditions (i.e., water, neutral pH) [Dowlut & Hall 2006; Berube et al. 2008; Tomsho and Benkovic 2012] compared to simple phenylboronic acid. However, the vacant p-orbital on boron—necessary for complexation with polyols—often complicates multistep syntheses of more complex derivatives.

Related compounds, benzoxaborins (2) have also been found to have biological and therapeutic applications, see International patent application WO2011116348.

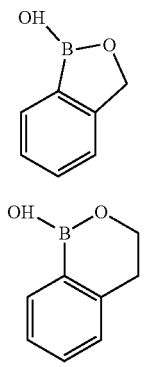

Ellis et al. 2012 have recently reported the use of boronic acids, particularly phenyl boronic acids and benzoxoboroles to enhance cytosolic delivery of proteins. Protecting groups for organoboronic acids and benzoxoboroles would be of interest for the synthesis of new biological and therapeutically active compounds.

There is also interest in the preparation of peptides derivatized with organoboronic acids and boroxoles, [Pal et al. 2010]. Protecting groups for organoboronic acids, benzoxaboroles and benzoxaborins that are compatible with solid-phase peptide synthesis would thus be of interest in the art.

The divalent protecting groups (a and b) are not suitable for protection of benzoxaboroles (e.g., 1) or benzoxaborins (e.g., 2) because they would result in anionic boronate complexes. Likewise fluoride protection (c) would yield potassium difluoroborate salt. While MIDA is suitable for protection of organoboronic acids, it is trivalent and not suitable for protection of benzoxaboroles or benzoxaborins, which only have two coordination sites.

The present invention provides divalent protecting groups for the protection of benzoxaboroles and structurally related trivalent protecting groups for the protection of organoboronic acids, particularly for phenylboronic acids. These protecting groups generate neutral adducts which are stable to a broad range of basic conditions, but which are readily deprotected under aqueous acidic conditions. The stability properties of the protecting groups of this invention complement the MIDA protecting group that is stable to a broad range of acidic conditions, but cleave under aqueous basic conditions.

SUMMARY OF THE INVENTION

The invention provides materials and methods for protecting organoboronic acids, including benzoxaboroles, benzoxaborins and phenylboronates, from undesired reaction. The invention provides di- and trivalent protecting groups which are prepared from precursor compounds of formula I:

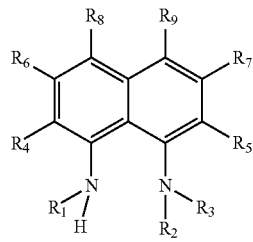

where:
$R_1$ is a methyl, ethyl or a —$(CH_2)_n$—OH group, where n is 2 or 3;
$R_2$ and $R_3$ are independently methyl or ethyl groups;
$R_4$ and $R_5$ are independently halogens or hydrogens;
$R_6$ and $R_7$ are independently hydrogens, halogens, or nitro groups; and
$R_8$ and $R_9$ are independently hydrogens, halogens or nitro groups or $R_8$ and $R_9$ together with a portion of the naphthalene ring form a 5-member ring, where when $R_1$ is —$CH_2$—$CH_2$—OH then the protecting group is a trivalent protecting group.

In specific embodiments, $R_1$ is a methyl or ethyl group and the protecting group formed is divalent. In specific embodiments, $R_1$-$R_3$ are all methyl groups. In specific embodiments, $R_1$ is —$(CH_2)_n$—OH, where n is 2 or 3, and the protecting group formed is trivalent. In specific embodiments, $R_2$ and $R_3$ are both methyl groups. In specific embodiments, $R_4$ and $R_5$ are both hydrogens. In specific embodiments, $R_6$ and $R_7$ are hydrogen or halogens. In specific embodiments, halogens are fluorines, chlorines or bromines. In specific embodiments, halogens are bromine. In specific embodiments, $R_6$ and $R_7$ are hydrogen or nitro groups.

In specific embodiments, protecting groups include those prepared from precursor compounds of formula II:

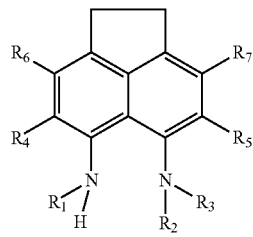

where variables are as defined above.

The compounds of the invention of formulas I and II are useful for preparing protecting groups for organoboronic acids, benzoxaboroles and benzoxaborins. Protecting groups of this invention are stable in acid (aq) and are cleaved in base. The protecting groups of this invention are complementary to the MIDA protecting groups which cleaves in base(aq) and not acid.

The invention further provides protected benzoxaboroles and benzoxaborins and protected organoboronic acids wherein the protecting group is a compound of formula I or II.

The invention provides protected benzoxaboroles and benzoxaborins of formula III:

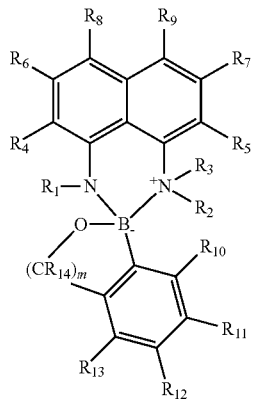

where $R_1$ is a methyl or ethyl group and $R_2$-$R_9$ are as defined above, m is 1 or 2, and $R_{10}$-$R_{13}$ and each $R_{14}$ is independently hydrogen, a non-hydrogen substituent or an organic group. In specific embodiments, $R_1$ is a methyl group. In specific embodiments, $R_1$-$R_3$ are all methyl groups. In specific embodiments, all of $R_4$-$R_9$ are hydrogens. In a specific embodiment, m is 1. In another specific embodiment, m is 2. In specific embodiments, each $R_{14}$ is independently hydrogen or an alkyl group having 1-3 carbon atoms.

The invention provides protected benzoxaboroles of formula IIIA:

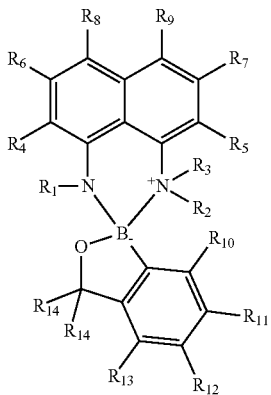

where variables are as defined for formula III. In specific embodiments, each $R_{14}$ is independently hydrogen or an alkyl group having 1-3 carbon atoms.

The invention provides protected organoboronic acids of formula IV:

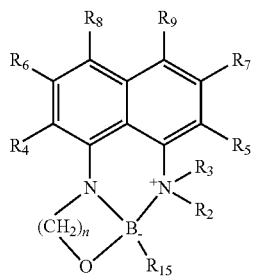

where variables are as defined above and $R_{15}$ is an organic group, wherein the bond between the B and $R_{15}$ is a boron-carbon bond. In specific embodiments, $R_2$ and $R_3$ are methyl groups. In specific embodiments, n is 2. In specific embodiments, all of $R_4$-$R_9$ are hydrogens.

The invention provides protected phenylboronic acids of formula IVA:

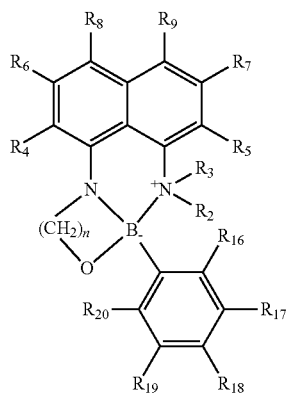

where variables are as defined in formulas I and IV and $R_{16}$-$R_{20}$ are independently selected from hydrogen, a non-hydrogen substituent or an organic group. In specific embodiments, $R_2$ and $R_3$ are methyl groups. In specific embodiments, n is 2. In specific embodiments, all of $R_4$-$R_9$ are hydrogens.

Organic groups of formulas III, IIIA, IV and IVA are optionally substituted with one or more non-hydrogen substituents.

The invention further provides methods for protecting organoboronic acids, or benzoxaboroles, and benzoxaborins employing trivalent or divalent protecting groups of formulas I or II, respectively.

The invention additionally provides methods of performing a chemical reaction in which an organoboronic acid, a benzoxaborole or a benzoxaborin is a reactant wherein the listed boron-containing reactant is protected with a protecting group of formula I or II or more specifically wherein the listed boron-containing reactant is a protected boron-containing compound of formula II, IIA, IV or IVA. In a specific embodiment, the chemical reaction is a cross-coupling reaction and more specifically is a Suzuki-Miyaura cross-coupling reaction.

DETAILED DESCRIPTION OF THE INVENTION

This invention is based at least in part on the preparation of stable adducts of trimethyl diaminonaphthalene with benzoxoborole derivatives:

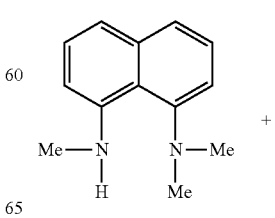

10

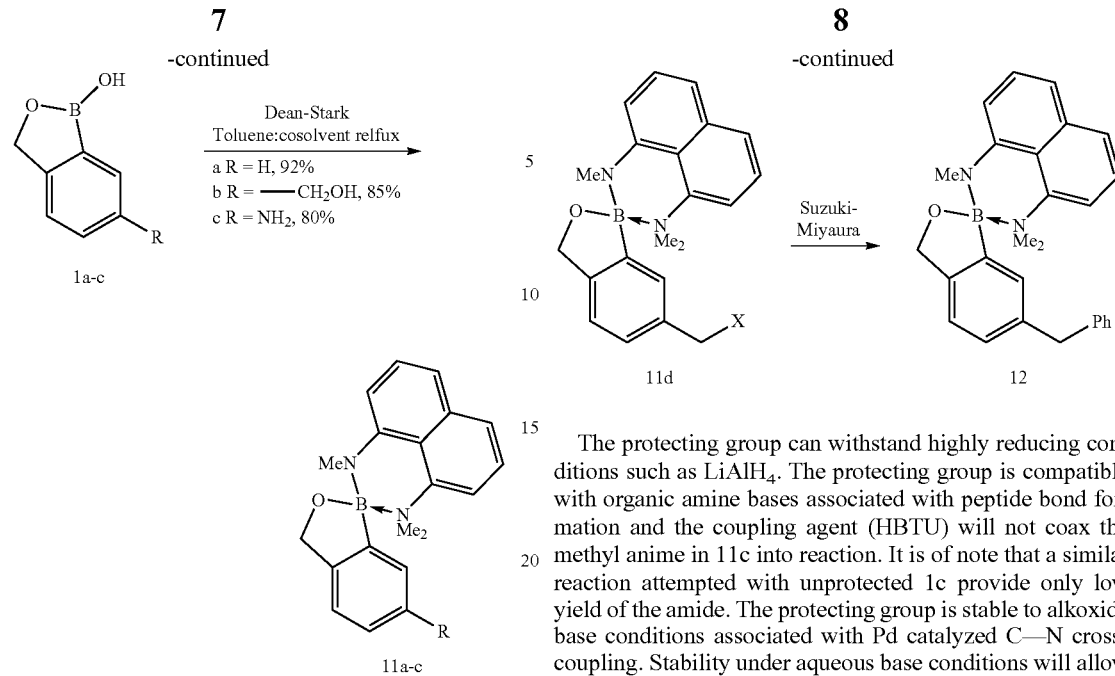

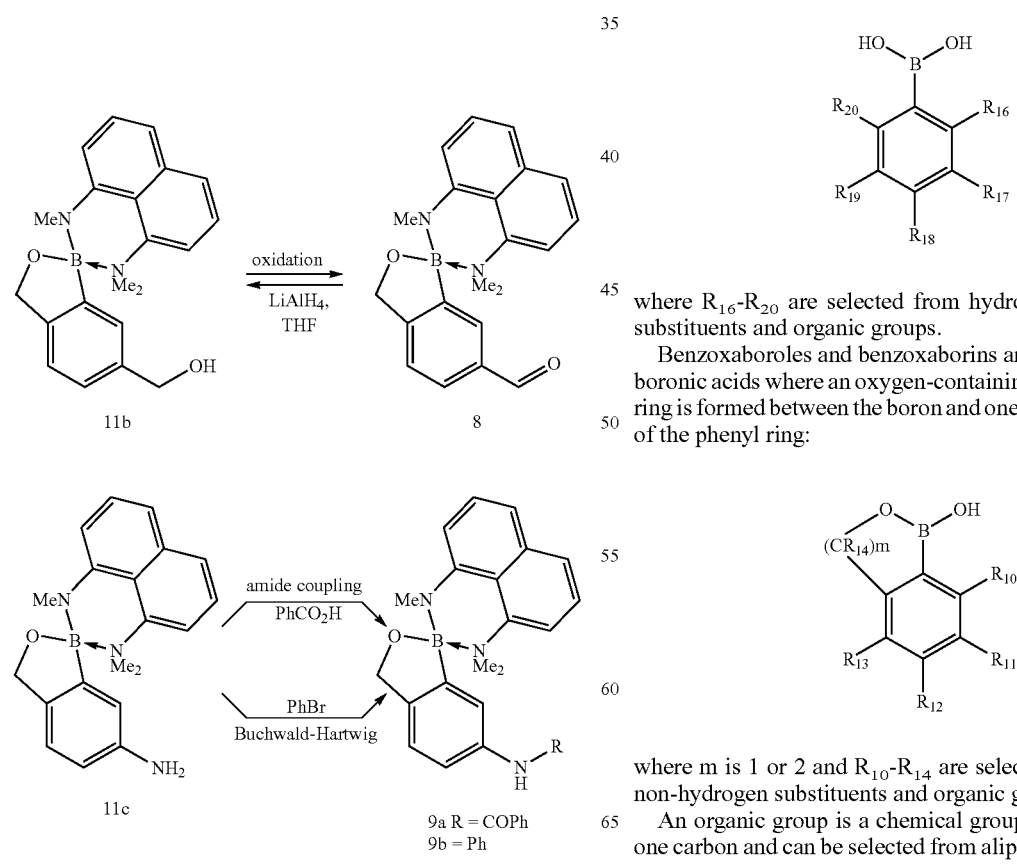

The adduct 11a was subjected to a screen of reaction conditions to determine its stability see Table 1. A general trend emerges that the adducts are completely stable to basic conditions while cleaving in acidic aqueous conditions.

Based on reactivity screens the protecting groups of this reaction will be useful in the reactions in Scheme 1:

The protecting group can withstand highly reducing conditions such as LiAlH$_4$. The protecting group is compatible with organic amine bases associated with peptide bond formation and the coupling agent (HBTU) will not coax the methyl anime in 11c into reaction. It is of note that a similar reaction attempted with unprotected 1c provide only low yield of the amide. The protecting group is stable to alkoxide base conditions associated with Pd catalyzed C—N cross-coupling. Stability under aqueous base conditions will allow for efficient Suzuki-Miyuara reaction, and facilitate iterative C—C cross-couplings (note that compound 1d and corresponding protected 11d represent the halides and pseudo halides used in the Suzuki-Miyuara coupling reaction).

The term organoboronic acid refers to a compound having formula: RX—B(OH)$_2$, where RX is and organic group bonded to B via a B—C bond. Phenyl boronic acids are organoboronic acids where a phenyl ring is bonded to the boron as in formula:

where R$_{16}$-R$_{20}$ are selected from hydrogen, non-hydrogen substituents and organic groups.

Benzoxaboroles and benzoxaborins are variants of phenyl boronic acids where an oxygen-containing 5- or 6-membered ring is formed between the boron and one of the ring positions of the phenyl ring:

where m is 1 or 2 and R$_{10}$-R$_{14}$ are selected from hydrogen, non-hydrogen substituents and organic groups.

An organic group is a chemical group containing at least one carbon and can be selected from aliphatic, alicyclic, aryl, heterocyclic, or heteroaryl groups, where when the organic group is bonded to the boron the bond is a C—B bond. Where the organic group is bonded to a carbon, the organic group can be bonded to the C through a C bond or a bond to oxygen, sulfur or nitrogen. Organic groups bonded to carbons include those bonded through the following linker moieties, —CO—, —O—CO—, —CO—O—, —NR—CO—, —CO—N—, —SO$_2$—NR—, —NR—SO$_2$—, —NR—CO—NR—, —O—, —S—, or —NR—, where R is H or an organic group and the linker is bonded to a carbon in the R group. Organic groups thus include, among others, oxy-, thio- or amino-aliphatic, oxy- or thio-alicyclic, oxy-, or thio-aryl groups. Organic groups are optionally substituted with non-hydrogen substituent groups as defined below.

In specific embodiments, organic groups are selected from alkyl, alkenyl, alkynyl, arylalkyl, aryl, alkoxy, alkenoxy, alkyoxy, arylalkoxy, aryloxy, thioalkyl, thioalkenyl, thioarylalkyl, thioaryl, carbocyclyl, heterocyclyl, heteroaryl, carbocyclyloxy, heterocyclyloxy, heteroaryloxy, thiocarbocyclyl, thioheterocyclyl, and thioheteroaryl. In additional embodiments organic groups which are bonded to carbons are selected from: —CO—R, —O—CO—R, —CO—O—R, —NR—CO—R, —CO—NR, —SO$_2$—NR—R, —NR—SO$_2$—R, —NR—CO—NR—R, —O—R, —S—R, or —NR—R, where each R independently is hydrogen or an organic group.

In specific embodiments, organic groups contain 1-100 carbon atoms, 1-50 carbon atoms, 1-25, carbon atoms, or 1-10 carbon atoms. In specific embodiments, organic groups contain 1-20 heteroatoms, 1-10 heteroatoms, 1-6 heteroatoms, or 1, 2, 3, 4, 5 or 6 heteroatoms. Heteroatoms include O, N, S, P or B and preferably are O, N or S.

In specific embodiments, an organic group is an optionally substituted alkyl group, an optionally substituted alkenyl group, an optionally substituted alkynyl group, an optionally substituted haloalkyl group, an optionally substituted haloalkenyl group, an optionally substituted haloalkynyl group, an optionally substituted vinyl group, an optionally substituted halovinyl group, an optionally substituted phenylvinyl group, an optionally substituted cyclohexylvinyl group, an optionally substituted cycloalkyl group, an optionally substituted aryl group, an optionally substituted phenylalkyl group, an optionally substituted phenyl group, an optionally substituted naphthyl group, an optionally substituted indenyl, or an optionally substituted biphenyl group.

In specific embodiments, an organic group is a cycloalkyl group having one or more 3-10 member rings which is optionally substituted. More specifically an organic group is cyclopropyl, cyclobutyl, cyclopentyl or cyclohexyl which is optionally substituted. In specific embodiments an organic group is a bicycloalkyl having 5-10 carbon atoms which is optionally substituted. In specific embodiments an organic group is a cycloalkenyl group having one or more 3-10 member rings which is optionally substituted. In specific embodiments an organic group is a bicycloalkenyl having 5-10 carbon atoms which is optionally substituted.

In specific embodiments, an organic group is an optionally substituted phenyl group, or an optionally substituted phenyl-substituted alkyl group, wherein the alkyl group has 1-6 carbon atoms. In specific embodiments, optional substitution of phenyl groups includes substitution with one or more halogen, hydroxyl, nitro, cyano, acetyl, formyl, trifluormethyl, alkyl (e.g., having 1-6 carbon atoms), alkoxy (e.g., having 1-6 carbon atoms), hydroxyalkyl (e.g., having 1-6 carbon atoms), vinyl groups, halovinyl groups, phenyl groups, halophenyl, benzyl, or halobenzyl. In specific embodiments, optional substitution of phenyl groups includes substitution with one, two or three of the listed groups. In specific embodiments, optional substitution of phenyl groups includes substitution with one, two, three, four or five halogen atoms.

In specific embodiments, an organic group is a heterocyclic or heteroaryl group which is optionally substituted. In specific embodiments, an organic group is a heterocyclic group having one 5- or 6-member ring having 1-3 heteroatoms in the ring, particularly N, O and/or S, and optionally 1 or 2 double bonds and wherein one or two ring carbons can be replaced with —CO— or —CS—. In specific embodiments, an organic group is a heterocyclic group having two rings which are fused wherein at least one ring is a 5- or 6-member ring having 1-3 heteroatoms in the ring, particularly N, O and/or S, and optionally 1 or 2 double bonds, wherein one or two ring carbons can be replaced with —CO— or —CS—, the other ring can be a 5-, or 6-member carbocyclic, aryl, heteroaryl or heterocyclic ring. In specific embodiments, an organic group is a heterocyclic group having two rings which are optionally fused, wherein both rings are 5- or 6-member rings having 1-3 heteroatoms in the ring, particularly N, O and/or S, and optionally 1 or 2 double bonds, wherein one or two ring carbons can be replaced with —CO— or —CS—. In specific embodiments, heterocyclic rings are substituted with one or more halogens, alkyl groups, phenyl groups or benzyl groups. Specific heterocyclic groups include oxiranyl, tetrahydrofuranyl, tetrahydropyranyl, pyrimidinyl, pyrrolidinyl, morpholinyl, thiomorpholinyl, piperidinyl, dioxanyl, dioxolanyl, a pyridinone group, or thianthrenyl, noting that the $R_{15}$ group is bonded to B through a C—B bond.

In specific embodiments, an organic group is a heteroaryl group having one or two rings at least one of which is aromatic and which are optionally fused wherein at least one ring is a 5- or 6-member ring having 1-3 heteroatoms in the ring, particularly N, O and/or S. Specific heteroaryl groups include, pyridyl, indoyl, pyrazolyl, thiophenyl, furanyl, quinolinyl, isoquinolinyl, benzofuranyl, thiazolyl, benzothiophenyl, pyrrolyl, benzimidazolyl, piperidinyl, triazolopyridyl, oxadiazolopyridyl, benzothiazolyl, benzothiadiazolyl, benzodioxanyl, 1-phenylpyrrolyl, indazolyl, 2,2'-bithiophenyl, 2,2':5,2"-terthiophenyl, dioxolylbenzyl, dihydronapthythyridinyl, or furylphenyl, noting that the organic group can be bonded through a B—C bond, a C—C bond or a heteroatom-C bond.

Organoboronic acids and variants thereof may include more than one —B(OH)$_2$ or variant boronate group.

In specific embodiments, organic groups include metal-containing groups, such as groups that contain metals, such as tin (Sn), zinc (Zn), silicon (Si), boron, and combinations thereof. In specific embodiments, non-hydrogen substituents include organic groups that contain metals, such as tin (Sn), zinc (Zn), silicon (Si), boron, and combinations thereof.

Non-hydrogen substituents include halogen, nitro, cyano, cyanate, azido, thiocyano, isocyano, isothiocyano, sulfhydryl, hydroxyl, alkyl, alkoxy, alkenyl, alkenyloxy, alkynyl, alkynyloxy, aryl, aryloxy, heteroaryl, heteroaryloxy, carbocyclyl, carbocyclyloxy, heterocyclyl, heterocyclyloxy, alkylthio, alkenylthio, alkynylthio, arylthio, heteroarylthio, heteroarylthio, carbocyclylthio, heterocyclylthio, —COR, —COH, —OCOR, —OCOH, —CO—OR, —CO—OH, —CO—O—CO—R, —CON(R)$_2$, —CONHR, —CONH$_2$, —NR—COR, —NHCOR, —NHR, —N(R)$_2$, —O—SO$_2$—R, —SO$_2$—R, —SO$_2$—NHR, —SO$_2$—N(R)$_2$, —NR—SO$_2$—R, —NH—SO$_2$—R, —NRCO—N(R)$_2$, —NH—CO—NHR, —O—PO(OR)$_2$, —O—PO(OR)(N(R)$_2$), —O—PO(N(R)$_2$)$_2$, —N—PO(OR)$_2$, —N—PO(OR)(N(R)$_2$), —P(R)$_2$, —B(OH)$_2$, —B(OH)(OR), —B(OR)$_2$, —O—Si(R)$_3$, or —SeR, where each R independently is an organic group and more specifically is an alkyl, alkenyl, alkynyl, aryl, heteroaryl, carbocyclyl, or heterocyclyl group or two R within the same substituent can together form a carbocyclic or heterocyclic ring having 3 to 10 ring atoms. Organic groups of non-hydrogen substituents are in turn optionally substituted with one or more halogens, nitro, cyano, isocyano, isothiocyano, hydroxyl, sulfhydryl, haloalkyl, hydroxyalkyl, amino, alkylamino, dialkylamino, arylalkyl, unsubstituted alkyl, unsubstituted alkenyl, unsubstituted alkynyl alkylalkenyl, alkylalkynyl, haloaryl, hydroxylaryl, alkylaryl, unsubstituted aryl, unsubstituted carbocylic, halo-substituted carbocyclic, hydroxyl-substituted carbocyclic, alkyl-substituted carbocyclic, unsubstituted heterocyclic, unsubstituted heteroaryl, alkyl-substituted heteroaryl, or alkyl-substituted heterocyclic. In specific embodiments, R groups of substituents are independently selected from alkyl groups, haloalkyl groups, phenyl groups, benzyl groups and halo-substituted phenyl and benzyl groups. In specific embodiments, non-hydrogen substituents have 1-20 carbon atoms, 1-10 carbon atoms, 1-7 carbon atoms, 1-5 carbon atoms or 1-3 carbon atoms. In specific embodiments, non-hydrogen substituents have 1-10 heteroatoms, 1-6 heteroatoms, 1-4 heteroatoms, or 1, 2, or 3 heteroatoms. Heteroatoms include O, N, S, P, B and Se and preferably are O, N or S.

In specific embodiments, organoboronic acids include those which are haloorganoboronic acids wherein the organic group contains a halogen. In specific embodiments, organoboronic acids include those which are pseudohaloorganoboronic acids wherein the organic group contains a pseudohalogen group, which is a group having chemical reactivity similar to a halogen group. Such groups include triflate ($-O-SO_2-CF_3$), methanesulfonate ($-O-SO_2-CH_3$), cyanate ($-O-C\equiv N$), azide ($-N_3$) thiocyanate ($-N=C=S$), alkylthio ($-S-R$), anhydride ($-CO-O-CO-R$), and phenyl selenide ($-Se-C_6H_5$).

In specific embodiments, $R_{15}$ is an alkyl group, an alkenyl group, an alkynyl group, a haloalkenyl group, a vinyl group, a halovinyl group, a phenylvinyl group, a cyclohexylvinyl group, a cycloalkyl group, an aryl group, a phenylalkyl group, an optionally substituted phenyl group, a naphthyl group, an indenyl, or a biphenyl group each of which is optionally substituted.

In specific embodiments $R_{15}$ is a cycloalkyl group having one or more 3-10 member rings which is optionally substituted. More specifically $R_{15}$ is cyclopropyl, cyclobutyl, cyclopentyl or cyclohexyl. In specific embodiments $R_{15}$ is a bicycloalkyl having 5-10 carbon atoms. In specific embodiments $R_{15}$ is a cycloalkenyl group having one or more 3-10 member rings which is optionally substituted. In specific embodiments $R_{15}$ is a bicycloalkenyl having 5-10 carbon atoms.

In specific embodiments, $R_{15}$ is an optionally substituted phenyl group, or an optionally substituted phenyl-substituted alkyl group, wherein the alkyl group have 1-6 carbon atoms. In specific embodiments, optional substitution of phenyl groups includes substitution with one or more halogen, hydroxyl, nitro, cyano, acetyl formyl, trifluormethyl, alkyl (e.g., having 1-6 carbon atoms), alkoxy (e.g., having 1-6 carbon atoms), hydroxyalkyl (e.g., having 1-6 carbon atoms), vinyl groups, halovinyl groups, phenyl groups, halophenyl, benzyl, or halobenzyl.

In specific embodiments, $R_{15}$ is a heterocyclic or heteroaryl group which is optionally substituted. In specific embodiments, $R_{15}$ is a heterocyclic group having one 5- or 6-member ring having 1-3 heteroatoms in the ring, particularly N, O and/or S, and optionally 1 or 2 double bonds and wherein one or two ring carbons can be replaced with $-CO-$ or $-CS-$. In specific embodiments, $R_{15}$ is a heterocyclic group having two rings which are fused wherein at least one ring is a 5- or 6-member ring having 1-3 heteroatoms in the ring, particularly N, O and/or S, and optionally 1 or 2 double bonds, wherein one or two ring carbons can be replaced with $-CO-$ or $-CS-$, the other ring can be a 5-, or 6-member carbocyclic, aryl, heteroaryl or heterocyclic ring. In specific embodiments, $R_{15}$ is a heterocyclic group having two rings which are optionally fused, wherein both rings are 5- or 6-member rings having 1-3 heteroatoms in the ring, particularly N, O and/or S, and optionally 1 or 2 double bonds, wherein one or two ring carbons can be replaced with $-CO-$ or $-CS-$. In specific embodiments, heterocyclic rings are substituted with one or more halogens, alkyl groups, phenyl groups or benzyl groups. Specific heterocyclic groups include oxiranyl, tetrahydrofuranyl, tetrahydropyranyl, pyrimidinyl, pyrrolidinyl, morpholinyl, thiomorpholinyl, piperidinyl, dioxanyl, dioxolanyl, a pyridinone group, or thianthrenyl, noting that the $R_{15}$ group is bonded to B through a C—B bond.

In specific embodiments, $R_{15}$ is a heteroaryl group having one or two rings at least one of which is aromatic and which are optionally fused wherein at least one ring is a 5- or 6-member ring having 1-3 heteroatoms in the ring, particularly N, O and/or S. Specific heteroaryl groups include, pyridyl, indoyl, pyrazolyl, thiophenyl, furanyl, quinolinyl, isoquinolinyl, benzofuranyl, thiazolyl, benzothiophenyl, pyrrolyl, benzimidazolyl, piperidinyl, triazolopyridyl, oxadiazolopyridyl, benzothiazolyl, benzothiadiazolyl benzodioxanyl, 1-phenylpyrrolyl, indazolyl, 2,2'-bithiophenyl, 2,2':5,2"-terthiophenyl, dioxolylbenzyl, dihydronapththyridinyl, or furylphenyl, noting that the $R_{15}$ group is bonded to B through a C—B bond.

In specific embodiments, one or more of $R_{10}$-$R_{14}$ or one or more of $R_{16}$-$R_{20}$ are independently an alkyl group, an alkenyl group, an alkynyl group, a haloalkenyl group, a vinyl group, a halovinyl group, a phenylvinyl group, a cyclohexylvinyl group, a cycloalkyl group, an aryl group, a phenylalkyl group, an optionally substituted phenyl group, a naphthyl group, an indenyl, or a biphenyl group each of which is optionally substituted.

In specific embodiments one or more of $R_{10}$-$R_{14}$ or one or more of $R_{16}$-$R_{20}$ is a cycloalkyl group having one or more 3-10 member rings which is optionally substituted. More specifically one or more of $R_{10}$-$R_{14}$ or one or more of $R_{16}$-$R_{20}$ is cyclopropyl, cyclobutyl, cyclopentyl or cyclohexyl. In specific embodiments one or more of $R_{10}$-$R_{14}$ or one or more of $R_{16}$-$R_{20}$ is a bicycloalkyl having 5-10 carbon atoms. In specific embodiments one or more of $R_{10}$-$R_{14}$ or one or more of $R_{16}$-$R_{20}$ is a cycloalkenyl group having one or more 3-10 member rings which is optionally substituted. In specific embodiments one or more of $R_{10}$-$R_{14}$ or one or more of $R_{16}$-$R_{20}$ is a bicycloalkenyl having 5-10 carbon atoms.

In specific embodiments, one or more of $R_{10}$-$R_{14}$ or one or more of $R_{16}$-$R_{20}$ is an optionally substituted phenyl group, or an optionally substituted phenyl-substituted alkyl group, wherein the alkyl group have 1-6 carbon atoms. In specific embodiments, optional substitution of phenyl groups includes substitution with one or more halogen, hydroxyl, nitro, cyano, acetyl formyl, trifluormethyl, alkyl (e.g., having 1-6 carbon atoms), alkoxy (e.g., having 1-6 carbon atoms), hydroxyalkyl (e.g., having 1-6 carbon atoms), vinyl groups, halovinyl groups, phenyl groups, halophenyl, benzyl, or halobenzyl.

In specific embodiments, one or more of $R_{10}$-$R_{14}$ or one or more of $R_{16}$-$R_{20}$ is a heterocyclic or heteroaryl group which is optionally substituted. In specific embodiments, one or more of $R_{10}$-$R_{14}$ or one or more of $R_{16}$-$R_{20}$ is a heterocyclic group having one 5- or 6-member ring having 1-3 heteroatoms in the ring, particularly N, O and/or S, and optionally 1 or 2 double bonds and wherein one or two ring carbons can be replaced with —CO— or —CS—. In specific embodiments, one or more of $R_{10}$-$R_{13}$ or one or more of $R_{16}$-$R_{20}$ is a heterocyclic group having two rings which are fused wherein at least one ring is a 5- or 6-member ring having 1-3 heteroatoms in the ring, particularly N, O and/or S, and optionally 1 or 2 double bonds, wherein one or two ring carbons can be replaced with —CO— or —CS—, the other ring can be a 5-, or 6-member carbocyclic, aryl, heteroaryl or heterocyclic ring. In specific embodiments, one or more of $R_{10}$-$R_{14}$ or one or more of $R_{16}$-$R_{20}$ is a heterocyclic group having two rings which are optionally fused, wherein both rings are 5- or 6-member rings having 1-3 heteroatoms in the ring, particularly N, O and/or S, and optionally 1 or 2 double bonds, wherein one or two ring carbons can be replaced with —CO— or —CS—. In specific embodiments, heterocyclic rings are substituted with one or more halogens, alkyl groups, phenyl groups or benzyl groups. Specific heterocyclic groups include oxiranyl, tetrahydrofuranyl, tetrahydropyranyl, pyrimidinyl, pyrrolidinyl, morpholinyl, thiomorpholinyl, piperidinyl, dioxanyl, dioxolanyl, a pyridinone group, or thianthrenyl, noting that the one or more of $R_{10}$-$R_{14}$ or one or more of $R_{16}$-$R_{20}$ groups can be bonded to the phenyl ring by a C—C or a heteroatom-C bond.

In specific embodiments, one or more of $R_{10}$-$R_{14}$ or one or more of $R_{16}$-$R_{20}$ is a heteroaryl group having one or two rings at least one of which is aromatic and which are optionally fused wherein at least one ring is a 5- or 6-member ring having 1-3 heteroatoms in the ring, particularly N, O and/or S. Specific heteroaryl groups include, pyridyl, indoyl, pyrazolyl, thiophenyl, furanyl, quinolinyl, isoquinolinyl, benzofuranyl, thiazolyl, benzothiophenyl, pyrrolyl, benzimidazolyl, piperidinyl, triazolopyridyl, oxadiazolopyridyl, benzothiazolyl, benzothiadiazolyl benzodioxanyl, 1-phenylpyrrolyl, indazolyl, 2,2'-bithiophenyl, 2,2':5,2"-terthiophenyl, dioxolylbenzyl, dihydronapththyridinyl, or furylphenyl, noting that noting that the one or more of $R_{10}$-$R_{14}$ or one or more of $R_{16}$-$R_{20}$ groups can be bonded to the phenyl ring by a C—C or a heteroatom-C bond.

In specific embodiments, optional substitution includes substitution with one or more halogen, hydroxyl, nitro, cyano, acetyl formyl, trifluoromethyl, alkyl (e.g., having 1-6 carbon atoms), alkoxy (e.g., having 1-6 carbon atoms), haloalkyl (e.g., having 1-6 carbon atoms, hydroxyalkyl (e.g., having 1-6 carbon atoms), vinyl groups, halovinyl groups, phenyl groups, halophenyl, benzyl, or halobenzyl.

Additional, benoxaborole and benzoxaborin compounds which can be protected by the methods and materials of this invention are found in U.S. application Ser. No. 13/745,731, filed Jan. 18, 2013, which is incorporated by reference herein in its entirety.

The term protecting group is used herein as broadly as the term is used in the art to refer to a chemical group that is introduced into a molecule by reaction with a function group to protect that function group from further reaction under a given set of reaction conditions, but which can be selectively removed (by deprotection) to regenerate that functional group when protection is no longer needed or desired. The invention provides new protecting groups for organoboronic acids, benzoxaboroles and benzoxaborins and describes methods for protecting and for removal of protection. It will be appreciated that a given organoboronic acid, benzoxaborole or benzoxaborin may contain more than one of such groups for which it would be useful to provide protection. In this regard, compounds of the invention can be employed to protect one or more than one boronate, benzoxaborole and/or benzoxaborin functionality in a given compound in need of such protection. It will also be appreciated that protection as described herein of boronate, benzoxaborole and/or benzoxaborin functionality may be combined with the use of other art-known protection strategies for protection of other functional groups. Thus, functional groups in organic groups and in non-hydrogen substituents of the compounds of this invention may be protected using art-known protecting groups and methods of providing such protection.

Protecting groups for such other functional groups can be selected as is well-known in the art for ease of addition to and removal from (protection and deprotection of) a given functional group and to be non-reactive (i.e., protective) under conditions in which protection is desired. A wide variety of protective groups is known in the art. See, for example, P. G. M. Wuts and T. W. Greene (2006) Greene's Protective Groups in Organic Synthesis, 4th Ed. (Wiley-Interscience) and P. J. Kocienski (2005) Protecting Groups, 3rd Ed. (Georg Thieme Verlag, New York, which provide a description of protecting groups for various functional groups and also provide a description of reagents for introduction of protecting groups and a description of how deprotection is achieved. These references are specifically incorporated by reference herein for the structure of protecting groups (particularly amine protecting groups) and for methods for protecting and deprotecting functional groups including amines.

Protective groups are often classified for the group which they protect, for example, the term amine protecting group refers to a protecting group that can be introduced into a molecule carrying an amine functional group to protect the amine group. The amine-protecting group is bonded to the nitrogen of the amine to form —NRPR, where PR is the protecting group and R is any other appropriate atom or group (e.g., hydrogen, alkyl group, aryl group etc.). Other classes of protecting groups include alcohol protecting groups, carbonyl protecting groups or carboxylic acid protecting groups. It is understood in the art, that a given protecting group may be useful for protecting different functional groups. In specific embodiments, herein, compounds of the invention may contain one or more protecting group in addition to the new protecting groups described herein.

In specific embodiments, organic groups and non-hydrogen substituents of protected boron-containing adducts of formulas II, IIA, IV and IVA may contain organic groups or non-hydrogen substituent that are sensitive to the acidic conditions used to remove the protective groups of this invention. It will be appreciated by one of ordinary skill in the art that such acid-sensitive organic groups and non-hydrogen substituents can be accommodated in the protected boron-containing adducts herein, if they are provided with appropriate protecting groups. Such protecting groups for acid-sensitive functional groups are known in the art and one of ordinary skill in the art can select from among such known protecting groups those that will be appropriate for such application. Acid-cleavable protecting groups include among others Boc protecting groups for amines, acetals and ketals for protecting carbonyls or alcohols.

The compounds of formulas I and II can be prepared by one of ordinary skill in the art in view of the descriptions herein and in view of methods known in the art from starting materials and reagents that are commercially available or which can be prepared from available starting materials by well-known methods. Additionally, one of ordinary skill in the art can apply routine adaptation of methods that are well-known in the art to the preparation of these compounds.

In general any organoboronic acid, any phenylboronic acid, any benzoxaborole or any benzoxaborin can be protected employing the protecting groups of this invention.

Many organoboronic acids, phenylboronic acids, benzoxaboroles and benzoxaborins are commercially available, can be prepared from available starting materials by well-known methods or can be prepared by routine adaptation of well-known methods. U.S. Pat. Nos. 5,594,111; 5,594,151; 5,623,055; 5,777,148; 5,744,627; 5,837,878; 6,156,884; 6,075,126; 6,124,471; 6,462,179 and 6,630,577 and references cited therein provide methods that can be employed to make organoboronic acids, phenylboronic acids, benzoxaboroles and benzoxaborins. Additionally, Snyder et al. 1958 and the Torssell references published in 1957 provide additional methods useful in the synthesis of boron-containing compounds.

Many organoboronic acids are commercially available, see for example, the Sigma-Aldrich catalogue (available at sigmaaldrich.com). See also, U.S. Pat. Nos. 8,013,203, 8,318,983 and 8,338,601 for additional synthetic methods. One of ordinary skill in the art can prepared organoboronic acids as well as benzoxaborole and benzoxaborin compounds of this invention in view of descriptions herein and in view of methods that are well-known in the art from available starting materials and reagents.

The terms alkyl or alkyl group refer to a monoradical of a straight-chain or branched saturated hydrocarbon. Alkyl groups include straight-chain and branched alkyl groups. Unless otherwise indicated alkyl groups have 1-20 carbon atoms (C1-C20 alkyl groups) and preferred are those that contain 1-10 carbon atoms (C1-C10 alkyl groups) or that contain 1-8 carbon atoms and more preferred are those that contain 1-6 carbon atoms (C1-C6 alkyl groups) and those that contain 1-3 carbon atoms (C1-C3 alkyl groups) Alkyl groups are optionally substituted with one or more non-hydrogen substituents as described herein. Exemplary alkyl groups include methyl, ethyl, n-propyl, iso-propyl, n-butyl, s-butyl, t-butyl, n-pentyl, branched-pentyl, n-hexyl, branched hexyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms.

A carbocyclyl group is a group having one or more saturated or unsaturated carbon rings. Carbocyclyl groups, for example, contain one or two double bonds. One or more carbons in a carbocyclic ring can be —CO— groups. Carbocyclyl groups include those having 3-12 carbon atoms, and optionally replacing 1 or 2 carbon atoms with a —CO— group and optionally having 1, 2 or 3 double bonds. Carbocyclyl groups include those having 5-6 ring carbons. Carbocyclyl groups can contain one or more rings each of which is saturated or unsaturated. Carbocyclyl groups include bicyclic and tricyclic groups. Preferred carbocyclic groups have a single 5- or 6-member ring. Carbocyclyl groups are optionally substituted as described herein. Specifically, carbocyclic groups can be substituted with one or more alkyl groups. Carbocyclyl groups include among others cycloalkyl and cycloalkenyl groups.

Cycloalkyl groups include those which have 1 ring or which are bicyclic or tricyclic. In specific embodiments, cycloalkyl groups have 1 ring having 5-8 carbon atoms and preferably have 5 or 6 carbon atoms.

Cycloalkenyl groups include those which have 1 ring or which are bicyclic or tricyclic and which contain 1-3 double bond. In specific embodiments, cycloalkenyl groups have 1 ring having 5-8 carbon atoms and preferably have 5 or 6 carbon atoms and have one double bond.

A heterocyclyl group is a group having one or more saturated or unsaturated carbon rings and which contains one to three heteroatoms (e.g., N, O or S) per ring. These groups optionally contain one, two or three double bonds. To satisfy valence requirement, a ring atom may be substituted as described herein. One or more carbons in the heterocyclic ring can be —CO— groups. Heterocyclyl groups include those having 3-12 carbon atoms, and 1-6, heteroatoms, wherein 1 or 2 carbon atoms are replaced with a —CO— group. Heterocyclyl groups include those having 3-12 or 3-10 ring atoms of which up to three can be heteroatoms other than carbon. Heterocyclyl groups can contain one or more rings each of which is saturated or unsaturated. Heterocyclyl groups include bicyclic and tricyclic groups. Preferred heterocyclyl groups have 5- or 6-member rings. Heterocyclyl groups are optionally substituted as described herein. Specifically, heterocyclic groups can be substituted with one or more alkyl groups. Heterocyclyl groups include those having 5- and 6-member rings with one or two nitrogens and one or two double bonds. Heterocyclyl groups include those having 5- and 6-member rings with an oxygen or a sulfur and one or two double bonds. Heterocyclyl group include those having 5- or 6-member rings and two different heteroatom, e.g., N and O, O and S or N and S. Specific heterocyclyl groups include among others among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups.

Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, and naphthyl groups, all of which are optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, pyridinyl, pyrazinyl, pyrimidinyl, quinolinyl, and purinyl groups. In specific embodiments herein aryl groups contain no heteroatoms in the aryl rings. Aryl including heteroaryl groups are optionally substituted.

Heteroatoms include O, N, S, P or B. More specifically heteroatoms are N, O or S. In specific embodiments, one or more heteroatoms are substituted for carbons in aromatic or carbocyclic rings. To satisfy valence any heteroatoms in such aromatic or carbocyclic rings may be bonded to H or a substituent group, e.g., an alkyl group or other substituent.

Arylalkyl groups are alkyl groups substituted with one or more aryl groups wherein the alkyl groups optionally carry additional substituents and the aryl groups are optionally substituted. Exemplary arylalkyl groups are benzyl groups.

Heteroarylalkyl groups are alkyl groups substituted with one or more heteroaryl groups wherein the alkyl groups optionally carry additional substituents and the aryl groups are optionally substituted.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

Alkylheteroaryl groups are heteroaryl groups substituted with one or more alkyl groups wherein the alkyl groups optionally carry additional substituents and the aryl groups are optionally substituted.

An alkoxy group is an alkyl group, as broadly discussed above, linked to oxygen ($R_{alkyl}$—O—). An aryloxy group is an aryl group, as discussed above, linked to an oxygen ($R_{aryl}$—O—). A heteroaryloxy group is a heteroaryl group as discussed above linked to an oxygen ($R_{heteroaryl}$—O—). A carbocyclyloxy group is an carbocyclyl group, as broadly discussed above, linked to oxygen ($R_{carbocyclyl}$—O—). A heterocyclyloxy group is an carbocyclyl group, as broadly discussed above, linked to oxygen ($R_{heterocyclyl}$—O—).

An acyl group is an R'—CO group where R' in general is a hydrogen, an alkyl, alkenyl or alkynyl, aryl or heteroaryl group as described above. In specific embodiments, acyl groups have 1-20, 1-12 or 1-6 carbon atoms and optionally 1-3 heteroatom, optionally one double bond or one triple bond. In specific embodiments, R is a C1-C6 alkyl, alkenyl or alkynyl group. cyclic configuration or a combination thereof, attached to the parent structure through a carbonyl functionality. Examples include acetyl, benzoyl, propionyl, isobutyryl, or oxalyl. The R' group of acyl groups are optionally substituted as described herein. When R' is hydrogen, the group is a formyl group. An acetyl group is a $CH_3$—CO— group. Another exemplary acyl group is a benzyloxy group.

An alkylthio group is an alkyl group, as broadly discussed above, linked to a sulfur ($R_{alkyl}$—S—) An arylthio group is an aryl group, as discussed above, linked to a sulfur ($R_{aryl}$—S—). A heteroarylthio group is a heteroaryl group as discussed above linked to an sulfur ($R_{heteroaryl}$—S—). A carbocyclylthio group is an carbocyclyl group, as broadly discussed above, linked to oxygen ($R_{carbocyclyl}$—S—). A heterocyclylthio group is an carbocyclyl group, as broadly discussed above, linked to oxygen ($R_{heterocyclyl}$—S—).

The term amino group refers to the species —N(H)$_2$—. The term alkylamino refers to the species —NHR" where R" is an alkyl group, particularly an alkyl group having 1-3 carbon atoms. The term dialkylamino refers to the species —NR$_2$" where each R" is independently an alkyl group, particularly an alkyl group having 1-3 carbon atoms.

Groups herein are optionally substituted most generally alky, alkenyl, alkynyl, and aryl, heteroaryl, carbocyclyl, and heterocyclyl groups can be substituted, for example, with one or more oxo group, thioxo group, halogen, nitro, cyano, cyanate, azido, thiocyano, isocyano, isothiocyano, sulfhydryl, hydroxyl, alkyl, alkoxy, alkenyl, alkenyloxy, alkynyl, alkynyloxy, aryl, aryloxy, heteroaryl, heteroaryloxy, carbocyclyl, carbocyclyloxy, heterocyclyl, heterocyclyloxy, alkylthio, alkenylthio, alkynylthio, arylthio, thioheteroaryl, thioheteroaryl, thiocarbocyclyl, thioheterocyclyl, —COR, —COH, —OCOR, —OCOH, —CO—OR, —CO—OH, —CO—O—CO—R, —CON(R)$_2$, —CONHR, —CONH$_2$, —NR—COR, —NHCOR, —NHR, —N(R)$_2$, —O—SO$_2$—R, —SO$_2$—R, —SO$_2$—NHR, —SO$_2$—N(R)$_2$, —NR—SO$_2$—R, —NH—SO$_2$—R, —NRCO—N(R)$_2$, —NH—CO—NHR, —O—PO(OR)$_2$, —O—PO(OR)(N(R)$_2$), —O—PO(N(R)$_2$)$_2$, —N—PO(OR)$_2$, —N—PO(OR)(N(R)$_2$), —P(R)$_2$, —B(OH)$_2$, —B(OH)(OR), —B(OR)$_2$, —O—Si(R)$_3$, or —SeR, where each R independently is an organic group and more specifically is an alkyl, alkenyl, alkynyl, aryl, heteroaryl, carbocyclyl, or heterocyclyl group or two R within the same substituent can together form a carbocyclic or heterocyclic ring having 3 to 10 ring atoms.

Organic groups of non-hydrogen substituents are in turn optionally substituted with one or more halogens, nitro, cyano, isocyano, isothiocyano, hydroxyl, sulfhydryl, haloalkyl, hydroxyalkyl, amino, alkylamino, dialkylamino, arylalkyl, unsubstituted alkyl, unsubstituted alkenyl, unsubstituted alkynyl alkylalkenyl, alkylalkynyl, haloaryl, hydroxylaryl, alkylaryl, unsubstituted aryl, unsubstituted carbocylic, halo-substituted carbocyclic, hydroxyl-substituted carbocyclic, alkyl-substituted carbocyclic, unsubstituted heterocyclic, unsubstituted heteroaryl, alkyl-substituted heteroaryl, or alkyl-substituted heterocyclic. In specific embodiments, R groups of substituents are independently selected from alkyl groups, haloalkyl groups, phenyl groups, benzyl groups and halo-substituted phenyl and benzyl groups. In specific embodiments, non-hydrogen substituents have 1-20 carbon atoms, 1-10 carbon atoms, 1-7 carbon atoms, 1-5 carbon atoms or 1-3 carbon atoms. In specific embodiments, non-hydrogen substituents have 1-10 heteroatoms, 1-6 heteroatoms, 1-4 heteroatoms, or 1, 2, or 3 heteroatoms. Heteroatoms include O, N, S, P, B and Se and preferably are O, N or S.

In specific embodiments, optional substitution is substitution with 1-12 non-hydrogen substituents. In specific embodiments, optional substitution is substitution with 1-6 non-hydrogen substituents. In specific embodiments, optional substitution is substitution with 1-3 non-hydrogen substituents. In specific embodiments, optional substituents contain 6 or fewer carbon atoms. In specific embodiments, optional substitution is substitution by one or more halogen, hydroxyl group, cyano group, oxo group, thioxo group, unsubstituted C1-C6 alkyl group or unsubstituted aryl group. The term oxo group and thioxo group refer to substitution of a carbon atom with a =O or a =S to form respectively —CO— (carbonyl) or —CS— (thiocarbonyl) groups.

In specific embodiments, substituents include organic groups (as defined herein) that contain metals, such as tin (Sn), zinc (Zn), silicon (Si), boron, and combinations thereof.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Compounds of the invention may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Salts of the invention include "pharmaceutically acceptable salts" which refers to those salts which retain the biological effectiveness and properties of the free bases or free acids, and which are not biologically or otherwise undesirable. Pharmaceutically acceptable salts comprise pharmaceutically-acceptable anions and/or cations.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

With respect to the various compounds of the invention, the atoms therein may have various isotopic forms, e.g., isotopes of hydrogen include deuterium and tritium. All isotopic variants of compounds of the invention are included within the invention and particularly included at deuterium and $^{13}C$ isotopic variants. It will be appreciated that such isotopic variants may be useful for carrying out various chemical and biological analyses, investigations of reaction mechanisms and the like. Methods for making isotopic variants are known in the art.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

Synthesis of 1-Dimethylamino-8-methylaminonaphthalenes

The following representative synthesis can be employed to prepare 1-dimethylamino-8-methylaminonaphthalenes, including those with further ring substitution, from corresponding 1,8-bis(dimethylamino)naphthalenes.

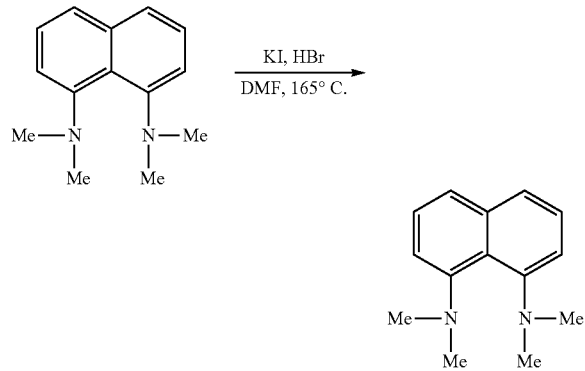

The divalent protecting group 1-dimethylamino-8-methylaminonaphthalene was synthesized using methods reported by Pozharskii and coworkers. [Ozeryanskii et al. 2005] A 250 mL round bottom flask was loaded with 1,8-bis(dimethylamino)naphthalene (1.071 g, 5 mmol) dissolved in 60 mL of DMF to which was added potassium iodide (4.15 g, 25 mmol), followed by HBr (0.25 mL, 46%). The reaction was refluxed with stirring for 1 hour, and then cooled to room temperature. The resulting slurry was poured into $dH_2O$ (625 mL), and was extracted with hexanes (15 mL×3), dried with $Na_2SO_4$, and concentrated by vacuum to a beige oil. No additional purification was required. (86%).

$^1$H-NMR (400 MHz, CDCl$_3$): δ ppm 8.94 (bs 1H, exchangeable with D$_2$O), 7.49 (dd 1H), 7.30 (t 1H), 7.29 (t 1H), 7.13 (dd 1H), 7.03 (dd 1H), 6.41 (bd 1H), 2.96 (d 3H), 2.76 (s 6H). $^{13}$C NMR (125 MHz, CDCl$_3$): δ 152, 148.1, 136.96, 127.08, 125.63, 125.35, 118.26, 115.14, 115.04, 102.60, 46.13, 30.5. HRMS (ESI) calcd. for $C_{13}H_{16}N_2$ [M+H] 201.1387. found 201.1391.

Example 2

Synthesis of Protected Benzoxaboroles and Benzoxaborins

The following representative methods can be employed for the preparation of protected benzoxaboroles and benzoxaborins of formula III. Protected benzoxaboroles and benzoxaborins can be prepared for example by reaction with the precursor to the protecting group in refluxing toluene (or toluene with a cosolvent) with removal of water, using for example a Dean-Stark trap.

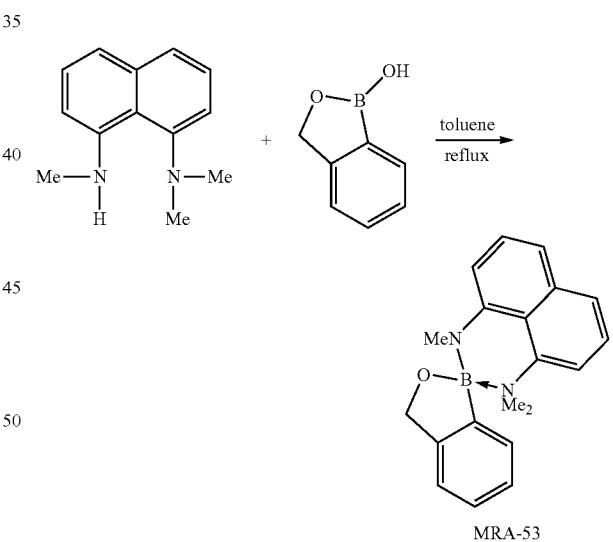

Synthesis of MRA-53

1-Dimethylamino-8-methylaminonaphthalene (0.540 g, 2.7 mmol), and (2-Hydroxymethyl)phenylboronic acid (0.120 g, 0.9 mmol) was dissolved in 20 mL of dry toluene. The reaction was fitted with a Dean-Stark trap (filled 5 mL dry toluene), and condensor, then heated at 125° C. for 24 h. The reaction was cooled to r.t., concentrated, redissolved into DCM (5 mL) and washed with a 2.5M NaOH solution (10 mL×3), dried with $Na_2SO_4$, and concentrated in vacuo to a brown oil. The residue was purified by column chromatography (1% MeOH in DCM) to provide MRA-53 (92%).

¹H-NMR (400 MHz, CDCl₃): δ ppm 7.79 (d 1H), 7.46 (t 1H), 7.38 (t 1H), 7.23 (bd 1H), 7.12 (m 2H), 6.78 (bt 1H), 6.61 (bd 1H), 6.14 (bs 1H), 5.22 (d 1H), 5.15 (d 1H), 2.92 (bs 3H), 2.87 (s 3H), 2.75 (s 3H). ¹³C NMR (125 MHz, CDCl₃): 149.17, 146.75, 143.66, 135.87, 129.00, 128.87, 128.58, 127.20, 126.13, 124.79, 120.14, 117.49, 113.32, 112.61, 105.43, 72.80, 46.29, 32.17. HRMS (ESI) calcd. for C₂₀H₂₁BN₂O [M+] 316.1857. found 316.1841.

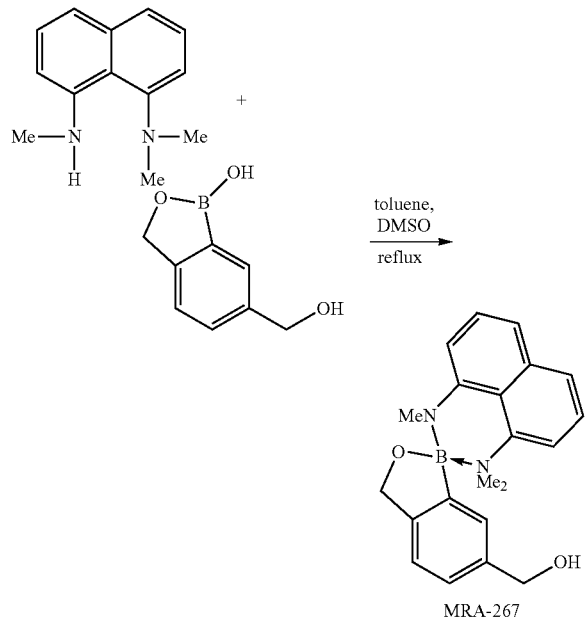

MRA-267

Synthesis of MRA-267

(2,4-Dihydroxymethyl)phenylboronic acid (0.164 g, 1 mmol) was dissolved in 1 mL of dry DMSO. 1-Dimethylamino-8-methylaminonaphthalene (0.6 g, 3 mmol), and 20 mL dry toluene was added. The reaction was fitted with a Dean-Stark trap (filled 5 mL dry toluene), and condensor, then heated at 130° C. for 24 h. The reaction was cooled to r.t., concentrated, redissolved into chloroform (5 mL) and washed with a 2.5M NaOH solution (10 mL×3), dried with Na₂SO₄, and concentrated in vacuo to a brown oil. The residue was purified by column chromatography (2.5% MeOH in DCM) to provide MRA-267 (85%).

¹H-NMR (400 MHz, CDCl₃): δ ppm 7.78 (d 1H), 7.46 (t 1H), 7.38 (t 1H), 7.37 (d 1H), 7.22 (d 1H), 7.17 (bd 1H), 7.13 (d 2H), 6.60 (d 1H), 5.21 (d 1H), 5.13 (d 1H), 4.29 (s 2H), 2.91 (bs 3H), 2.87 (s 3H), 2.75 (s 3H). ¹³C NMR (125 MHz, CDCl₃): 149.08, 146.57, 143.52, 138.54, 135.90, 129.01, 128.69, 127.76, 127.22, 126.83, 124.82, 120.43, 117.35, 113.45, 112.62, 105.37, 97.83, 72.58, 65.86, 46.11. HRMS (ESI) calcd. for C₂₁H₂₄BN₂O₂ [M+] 346.1962. found 346.1972.

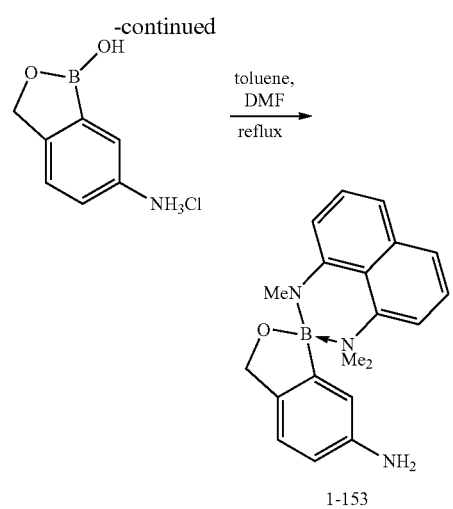

1-153

Synthesis of 1-153

5-Amino-2-hydroxymethylphenylboronic acid-HCl salt (0.5 g, 2.7 mmol) was dissolved in 3 mL of DMF, 3 mL of NEt₃, and a few drops of water and stirred for 1 h rt. 1-Dimethylamino-8-methylaminonaphthalene (1 g, 5.4 mmol) was added as a solution in 5 mL of toluene and the volatiles were removed in vacuo. The residue was dissolved in 50 mL of toluene and refluxed under Dean-Stark conditions for 12 h. The volatiles were removed in vacuo and the residue was purified by silica gel chromatography (95:5, DCM:MeOH) to give 1-153 (80%) and quantitative re-isolation of 1-Dimethylamino-8-methylaminonaphthalene.

¹H NMR (CDCl₃, 500 MHz) δ 7.76 (d, J=8.5 Hz, 1H), 7.46 (dd, app t, J=8, 8 Hz, 1H), 7.37 (dd, app t, J=8, 8 Hz, 1H), 7.22 (d, J=7.5 Hz, 1H), 7.11 (d, J=8 Hz, 1H), 6.91 (d, J=8 Hz, 1H), 6.60 (d, J=8 Hz, 1H), 6.49 (dd, J=8, 2 Hz, 1H), 5.49 (br s, 1H, H'), 5.14 (d, J=13 Hz, 1H), 5.06 (d, J=13 Hz, 1H), 2.89 (s, 3H), 2.87 (s, 3H), 2.76 (s, 3H). ¹³C NMR (CDCl₃, 100 MHz) δ 146.6, 144.2, 143.6, 139.7, 135.8, 128.9, 128.4, 124.8, 120.6, 117.3, 115.3, 115.1, 113.1, 112.6, 105.2, 72.4, 50.1, 44.3, 32.1. HRMS (ESI) calcd. for C₂₀H₂₂BN₃O [M+H] 331.1966. found 331.1967.

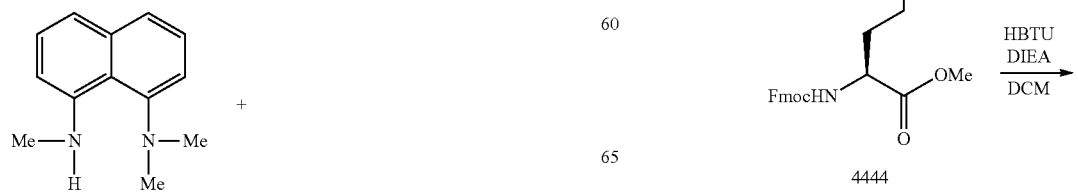

4444

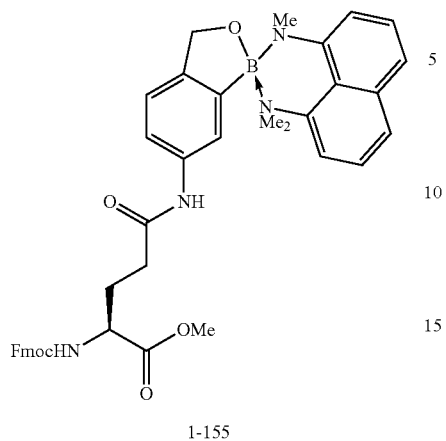

1-155

1-157

Synthesis of 1-155

Compound 1-153 (1.14 g, 3.44 mmol), compound 4444 (N-9-fluorenylmethoxycarbonylglutamic acid α-methyl ester, commercially available) (1.72 g, 4.47 mmol), and HBTU (1.96 g, 5.16 mmol) were dissolved in 50 mL of DCM:DMF (8:2). DIEA (1.78 g, 13.8 mmol) was added and the reaction stirred for 8 h. The volatiles were removed in vacuo and the residue was dissolved in DCM and extracted with sat. NH$_4$Cl (2×), sat. NaHCO$_3$ (2×) and water (2×). The organic layer was dried over Na$_2$SO$_4$ and evaporated to dryness. The residue was purified by silica gel chromatography (8:2, EtOAc:Hex) to give 1-155.

$^1$H NMR (CDCl$_3$, 500 MHz) δ 7.79-7.05 (m, 15H), 6.59 (d, J=7.5 Hz, 1H), 5.81 (br s, 1H), 5.78 (d, J=5 Hz, 1H), 5.17 (d, J=13.5 Hz, 1H), 5.08 (m, 1H), 4.35-4.2 (m, 3H), 4.17 (m, 1H), 3.69-2.85 (m, 9H), 2.15 (br m, 2H), 1.99-1.89 (m, 2H). $^{13}$C NMR (CDCl$_3$, 100 MHz) δ 172.5, 169.9, 156.4, 146.5, 145.3, 143.93, 143.91, 143.8, 143.4, 141.4, 136.0, 135.8, 129.0, 128.6, 127.8, 127.22, 127.20, 127.17, 125.3, 125.23, 125.20, 124.9, 120.7, 120.12, 120.11, 120.05, 119.9, 119.5, 117.2, 113.3, 112.8, 112.7, 105.4, 72.5, 66.94, 66.91, 53.6, 53.5, 52.7, 50.0, 47.3, 44.5, 33.4, 33.3, 32.2, 28.5, 28.4. HRMS (ESI) calcd. for C$_{41}$H$_{41}$BN$_4$O$_6$ [M+H] 696.3229. found 696.3253.

Synthesis of 1-157

The method of Capricciotti et al. 2011 which is incorporated by reference herein in its entirety was employed.

$^1$H NMR (DMSO-d$_6$, 500 MHz) δ 12.75 (br s, 1H), 7.96-6.89 (m, 15H), 6.47 (d, J=8 Hz, 1H), 4.97 (br s, 2H), 4.30-4.15 (m, 3H), 3.85 (m, 1H), 2.80-2.60 (diastereomeric Me, 9H), 2.20 (br t, 2H), 1.95 (m, 1H), 1.74 (m, 1H). $^{13}$C NMR (DMSO-d$_6$, 100 MHz) δ 176.0, 174.5, 170.1, 156.0, 151.9, 147.6, 146.0, 144.1, 143.9, 143.8, 143.3, 140.8, 137.1, 136.5, 135.2, 128.5, 128.0, 127.7, 127.1, 127.0, 125.5, 125.4, 125.3, 125.2, 125.0, 120.2, 120.1, 119.1, 117.5, 116.7, 115.1, 114.4, 113.9, 113.1, 104.4, 102.2, 71.5, 69.7, 65.6, 54.1, 49.9, 46.7, 45.7, 44.7, 32.7, 32.2, 30.1, 27.0. HRMS (ESI) calcd. for C$_{40}$H$_{39}$BN$_4$O$_6$ [M+H] 682.3072. found 682.3077.

Example 3

Synthesis of 1-Dimethylamino-8-(2-hydroxyethyl) aminonaphthalenes

The following representative synthesis can be employed to prepare 1-dimethylamino-8-(2-hydroxyethyl)aminonaphthalenes, including those with further ring substitution, from corresponding 1-di methylamino-8-methylaminonaphthalenes.

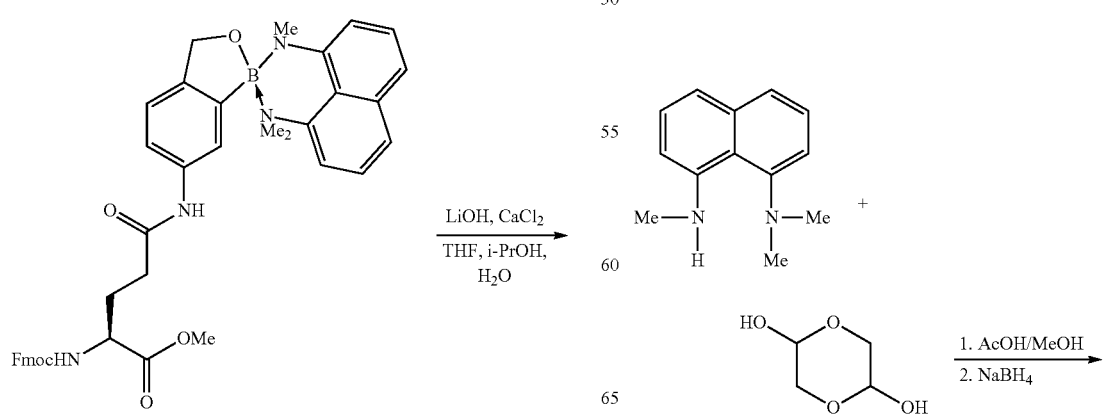

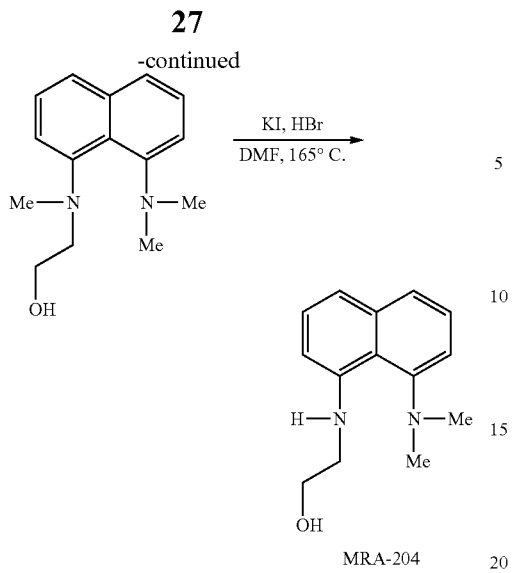

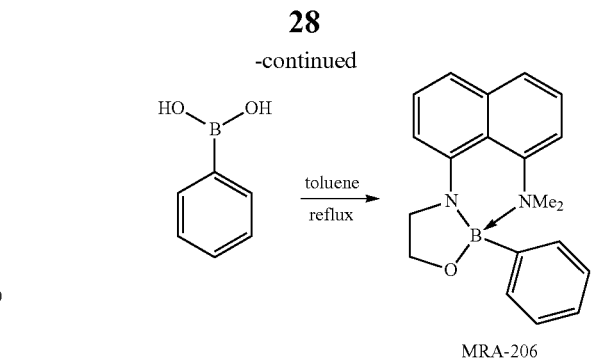

MRA-206

Synthesis of MRA-206

Phenylboronic acid (0.086 g, 0.7 mmol) and MRA-204 (0.065 g, 0.282 mmol) were dissolved in 10 mL of dry toluene. The reaction was fitted with a Dean-Stark trap (filled 5 mL dry toluene), and condensor, then heated at 125° C. for 24 h. The reaction was cooled to r.t., concentrated, redissolved into DCM (5 mL) and washed with a 2.5M NaOH solution (10 mL×3), dried with $Na_2SO_4$, and concentrated in vacuo to a tan solid. This was purified by column chromatography (1% MeOH in DCM) to provide MRA-206 (89.2%).

$^1$H-NMR (400 MHz, $CDCl_3$): d ppm 7.73 (d 1H), 7.48 (t 1H), 7.31 (t 1H), 7.25 (d 1H), 7.22 (d 2H), 7.12 (t 1H), 7.07 (t 3H), 6.58 (d 1H), 4.26 (dt 1H), 4.15 (dd 1H), 3.78 (dd 1H), 3.15 (m 1H), 2.97 (s 3H), 2.76 (s 3H). $^{13}$C NMR (125 MHz, $CDCl_3$): 149.91, 146.36, 141.41, 136.21, 132.91, 129.41, 128.71, 127.29, 124.61, 116.16, 113.96, 112.69, 104.10, 66.16, 59.82, 44.69, 31.46. HRMS (ESI) calcd. for $C_{20}H_{21}BN_2O$ [M+] 316.1857. found 316.1869.

Synthesis of MRA-204

1-Dimethylamino-8-methylaminonaphthalene (0.20 g, 1 mmol), and glycolaldehyde dimer (0.120 g, 1 mmol) was dissolved in 50/50 MeOH/AcOH (10 mL) and stirred 0/N. The solution was concentrated in vacuo with the addition of benzene (5 mL). The resulting pink solid was dissolved in anhydrous MeOH (10 mL), and treated with excess $NaBH_4$, and stirred 0/N. The reaction was concentrated, triturated in chloroform, filtered, and concentrated. The resulting solid was dissolved in DMF (12.5 mL), along with KI (0.883 g, 5 mmol) and HBr (0.12 mL, 1 mmol). The solution was heated to 165° C. for 45 min, cooled to r.t., and poured into $dH_2O$ (125 mL). The product was extracted into ether (3×25 mL), dried with $Na_2SO_4$, and concentrated. If necessary, the residue was purified by column chromatography (1:1 EtOAc: Hex) to provide MRA-204 (40% overall).

2 conformations represented, $^1$H-NMR (400 MHz, $CDCl_3$): d ppm 7.60 (d 1H), 7.51 (d 1H), 7.33 (m 5H), 7.17 (d 1H), 7.14 (d 1H), 7.07 (d 1H), 6.53 (d 1H), 6.50 (d 1H), 3.94 (t 2H), 3.58 (m 2H), 3.47 (t 2H), 3.22 (m 2H), 2.95 (s 3H), 2.78 (s 3H), 2.76 (s 6H). $^{13}$C NMR (125 MHz, MeOH): 153.43, 152.81, 149.46, 148.22, 138.59, 138.52, 128.05, 127.90, 127.16, 126.57, 126.45, 126.41, 120.71, 119.85, 118.89, 116.65, 116.57, 116.42, 104.59, 104.22, 61.73, 60.55, 60.23, 46.97, 46.39, 44.66, 30.73. HRMS (ESI) calcd. for $C_{14}H_{18}N_2O$ [M+1] 231.1492. found 231.1493.

Example 4

Synthesis of Protected Organoboronic Acids

The following representative methods can be employed for the preparation of protected organoboronic acids of formula IV.

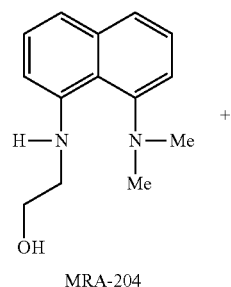

MRA-204

Example 5

Protecting Group Stability Tests

Stability tests of the protecting groups of this invention were conducted under selected reaction conditions using a representative protected organoboronic (M206) acid and a representative protected benzoxaborole (M53). The results are summarized in Table 1.

TABLE 1

Summary of Protecting Group Stability Tests for Representative Protected benzoxaborole (MRA-53) and Representative Protected organoboronic acid (MRA-206)

| | % Cleaved | Time (h) |
|---|---|---|
| Cleavage/Stability By$^1$ H NMR MRA-53(11a) | | |
| 10% $H_2O$ in $CHCl_3$ | 7 | 72 |
| 20% Piperdine in $CH_2Cl_2$ | 0 | 72 |
| 20% DIEA in $CH_2Cl_2$ | 0 | 72 |
| 0.5 NaOH in (THF/$H_2O$, 1:1) | 0 | 72 |
| Cleavage/Stability By LCMS MRA-53(11a) | | |
| 0.5M HCl in (THF/$H_2O$, 1:1) | 91 | 4 |
| 0.5M AcOH in (THF/$H_2O$, 1:1) | 56 | 4 |
| 0.5M $BF_3OEt_2$ in DCM | 98 | 48 |
| 4M HCl in dioxane | 70 | 48 |
| 0.5M TFA in DCM | 99 | 48 |
| MRA-206 | | |
| 0.5M HCl in (THF/$H_2O$, 1:1) | 100 | 30 min |
| 0.5 NaOH in (THF/$H_2O$, 1:1) | 0 | 72 hrs |

Example 6

Adducts of Related Ligands

The following divalent ligands do not form adducts with benzoxaole under Dean-Starke conditions that survive chromatography: 8-(dimethylamino)naphthalene-1-ol, N-methylquinoline-8-amine, quinolin-8-ol, quinolone-8-carboxylic acid, benzo[h]quinolin-10-ol, $N^1,N^1,N^2$-trimethylbenzene-1,2-diamine, or N-methylbenzo[h]quinolin-10-amine.

REFERENCES

Adamczyk-Woźniaka, M. K. Cyrańskib, A. Żubrowskaa, A. Sporzyńskia (2009) Benzoxaboroles-Old compounds with new applications, J. Organometallic Chem. 694(22):3533-3541.

Akama, T.; Baker, S. J.; Zhang, Y. K.; Hernandez, V.; Zhou, H.; Sanders, V.; Freund, Y.; Kimura, R.; Maples, K. R.; Plattner, J. J. Bioorg. Med. Chem. Lett. 2009, 19, 2129.

Baker, S. J.; Ding, C. Z.; Akama, T.; Zhang, Y. K.; Hernandez, V.; Xia, Y. Future Med. Chem. 2009, 1, 1275.

Baker, S. J.; Tomsho, J. W.; Benkovic, S. J. Chem. Soc. Rev. 2011, 40, 4279.

Berube, M.; Dowlut, M.; Hall, D. G. (2008) Benzoboroxoles as efficient glycopyranoside-binding agents in physiological conditions: Structure and selectivity of complex formation. J. Org. Chem., 73 (17), 6471-6479.

Capicciotti, C. J.; Trant, J. F.; Leclère, M.; Ben, R. N. Bioconjugate Chem., 2011, 22, 605-616.

Ding, D.; Meng, Q.; Gao, G.; Zhao, Y.; Wang, Q.; Nare, B.; Jacobs, R.; Rock, F.; Alley, M. R.; Plattner, J. J.; Chen, G.; Li, D.; Zhou, H. J. Med. Chem. 2011, 54, 1276.

Dixon, D. D.; Lockner, J. W.; Zhou, Q.; Baran, P. S. J. Am. Chem. Soc. 2012, 134, 8432.

Dowlut, M.; Hall, D. G. (2006) An improved class of sugar-binding boronic acids, soluble and capable of complexing glycosides in neutral water. J. Am. Chem. Soc., 128 (13), 4226-4227.

G. A. Ellis, M. J. Palte, and R. T. Raines (February 2012) Boronate-Mediated Biologic Delivery, J. Amer. Chem. Soc. 134:3631-3634.

Gillis, E. P.; Burke, M. D. Aldrichimica acta 2009, 42, 17.

Gillis, E. P.; Burke, M. D. J. Am. Chem. Soc. 2007, 129, 6716.

Gillis, E. P.; Burke, M. D. J. Am. Chem. Soc. 2008, 130, 14084.

H. Noguchi, K. Hojo, M. Suginome (2007) Boron-Masking Strategy for the Selective Synthesis of Oligoarenes via Iterative Suzuki-Miyaura Coupling, J. Am. Chem. Soc., 129, 758-759.

H. Noguchi, T. Shioda, C.-M. Chou, M. Suginome (2008) Differentially Protected Benzenediboronic Acids Divalent Cross-Coupling Modules for the Efficient Synthesis of Boron-Substituted Oligoarenes, Org. Lett., 10, 377-380.

Jacobs, R. T.; Plattner, J. J.; Nare, B.; Wring, S. A.; Chen, D.; Freund, Y.; Gaukel, E. G.; Orr, M. D.; Perales, J. B.; Jenks, M.; Noe, R. A.; Sligar, J. M.; Zhang, Y. K.; Bacchi, C. J.; Yarlett, J.; Don, R. (2011) Benzoxaboroles: A new class of potential drugs for human African trypanosomiasis. Future Med. Chem., 3, 1259-1278.

James, T. D. (2005) Boronic acid-based receptors and sensors for saccharides, In Boronic Acids; Hall, D. G., Ed.; Wiley-VCH Verlag GmbH & Co. KGaA: Weinheim, pp 441-479.

Kim, H.; Kang, Y. J.; Kang, S.; Kim, K. T. J. Am. Chem. Soc. 2012, 134, 4030.

Knapp, D. M.; Gillis, E. P.; Burke, M. D. J. Am. Chem. Soc. 2009, 131, 6961.

Li, X.; Zhang, Y. K.; Liu, Y.; Ding, C. Z.; Li, Q.; Zhou, Y.; Plattner, J. J.; Baker, S. J.; Qian, X.; Fan, D.; Liao, L. Ni, Z. J.; White, G. V.; Mordaunt, J. E.; Lazarides, L. X.; Slater, M. J.; Jarvest, R. L.; Thommes, P.; Ellis, M.; Edge, C. M.; Hubbard, J. A.; Somers, D.; Rowland, P.; Nassau, P.; McDowell, B.; Skarzynski, T. J.; Kazmierski, W. M.; Grimes, R. M.; Wright, L. L.; Smith, G. K.; Zou, W.; Wright, J.; Pennicott, L. E. Bioorg. Med. Chem. Lett. 2010, 20, 3550.

Molander, G. A.; Ellis, N. Acc. Chem. Res. 2007, 40, 275.

Molander, G. A.; Jean-Gérard, L., Organotrifluoroborates: Organoboron Reagents for the Twenty-First Century. In Boronic Acids, Wiley-VCH Verlag GmbH & Co. KGaA 2011; pp 507-550.

N. Miyaura and A. Suzuki (1995) Palladium-Catalyzed Cross-Coupling Reactions of Organoboron Compounds, Chem. Rev., 95:2457-2483.

Nishiyabu, R.; Kubo, Y.; James, T. D.; Fossey, J. S. (2011) Boronic acid building blocks: Tools for sensing and separation. Chem. Commun. 2011, 47, 1106-1123.

Obrecht, D.; Bernardini, F.; Dale, G.; Dembowsky, K., Chapter 15-Emerging New Therapeutics Against Key Gram-Negative Pathogens. In Annual Reports in Medicinal Chemistry, John, E. M., Ed. Academic Press 2011; Vol. Volume 46, pp 245-262.

Ozeryanskii, V. A.; Pozharskii, A. F. (2000) Peri-naphthylenediamines 29. 1,8-bis(dimethylamino)-3-nitro- and -3,6-dinitronaphthalenes and 5,6-bis(dimethylamino)-3-nitro- and -3,8-dinitroacenaphthenes as the first representatives of "proton sponges" meta-substituted relative to NMe2 groups, Russian Chemical Bulletin (Translation of Izvestiya Akademii Nauk, Seriya Khimicheskaya) (2000), 49(8), 1399-1405.

Ozeryanskii, V. A.; Pozharskii, A. F.; Koroleva, M. G.; Shevchuk, D. A.; Kazheva, O. N.; Chekhlov, A. N.; Shilov, G. V.; Dyachenko, O. A. (2005) N,N,N'-Trialkyl-1,8-diaminonaphthalenes: convenient method of preparation from protonated proton sponges and the first X-ray information, Tetrahedron, 61(17), 4221-4232.

Pal, A.; Berube, M.; Hall, D. H. (2010) Design, synthesis, and screening of a library of peptidyl bis(boroxoles) as oligosaccharide receptors in water: identification of a receptor for the tumor marker TF-antigen disaccharide, Angew. Chem., Int. Ed., 49, 1492-1495.

Pozharskii, A. F.; Kuz'menko, V. V.; Aleksandrov, G. G.; Dmitrienko, D. V. (1995) 1,8-Bis(dimethylamino)naphthalene. XIII. Solvatochromism and molecular structure of 4-nitro-1,8-bis(dimethylamino)naphthalene and its salt with perchloric acid Zhurnal Organicheskoi Khimii (1995), 31(4), 570-81.

Qiao, Z.; Wang, Q.; Zhang, F.; Wang, Z.; Bowling, T.; Nare, B.; Jacobs, R. T.; Zhang, J.; Ding, D.; Liu, Y.; Zhou, H. J. Med. Chem. 2012, 55, 3553.

Rock, F. L.; Mao, W.; Yaremchuk, A.; Tukalo, M.; Crepin, T.; Zhou, H.; Zhang, Y. K.; Hernandez, V.; Akama, T.; Baker, S. J.; Plattner, J. J.; Shapiro, L.; Martinis, S. A.; Benkovic, S. J.; Cusack, S.; Alley, M. R. Science 2007, 316, 1759.

Snyder, H. R.; Reedy, A. J.; Lennarz, W. J. Synthesis of Aromatic Boronic Acids—Aldehydro Boronic Acids and a Boronic Acid Analog of Tyrosine. J. Am. Chem. Soc. 1958, 80 (4), 835-838.

Tomsho, J. W.; Benkovic, S. J. J. Org. Chem. 2012, 77, 11200.

Tomsho, J. W., Pal, A., Hall, D. G. and Benkovic S. J. Ring Structure and Aromatic Substituent Effects on the pKa of the Benzoxaborole Pharmacophore, ACS Med. Chem. Letts. 3(1):48-52 (2012) published on-line Oct. 19, 2011.

Torssell, K. Arylboronic acids I. Arkiv foer Kemi 10:473-482 (1957).

Torssell, K. Arylboronic acids II. Arkiv foer Kemi 10:497-505 (1957).

Torssell, K. Arylboronic acids III. Bromination of tolylboronic acids according to Wolf-Ziegler. Arkiv foer Kemi 10:507-511 (1957).

Torssell, K. Arylboronic acids IV. Nitration of several arylboronic acids and characteristics of the boron-carbon bond. Arkiv foer Kemi 10:513-521 (1957).

Torssell, K. Arylboronic acids. A review. Svensk Kemisk Tidskrift 69:34-44 (1957).

Torssell, K. Arylboronic acids. V. Effects of arylboronic acids on microorganisms and enzymes. Arkiv. Kemie 10:529-540 (1957).

Torssell, K. Arylboronic acids. VII. Complex formation between phenylboronic acid and fructose. Arkiv foer Kemie 10:541-547 (1957).

Xia, Y.; Cao, K.; Zhou, Y.; Alley, M. R.; Rock, F.; Mohan, M.; Meewan, M.; Baker, S. J.; Lux, S.; Ding, C. Z.; Jia, G.; Kully, M.; Plattner, J. J. Bioorg. Med. Chem. Lett. 2011, 21, 2533.

Yang, W., Gao, X., Wang, B. (2005) Biological and medicinal applications of boronic acids, In Boronic Acids; Hall, D. H., Ed.; Wiley-VCH Verlag GmbH & Co. KGaA: Weinheim, pp 481-512.

Zhdankin, V. V.; Persichini, P. J.; Zhang, L.; Fix, S.; Kiprof, P. (1999) Synthesis and structure of benzoboroxoles: Novel organoboron heterocycles. Tetrahedron Lett. 1999, 40 (37), 6705-6708.

The invention claimed is:

1. A protected organoboronic acid of formula:

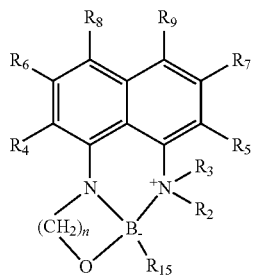

where:
n is 2 or 3;
$R_2$ and $R_3$ are independently methyl or ethyl groups;
$R_4$ and $R_5$ are independently halogens or hydrogens;
$R_6$ and $R_7$ are independently hydrogens, halogens, or nitro groups; and
$R_8$ and $R_9$ are independently hydrogens, halogens or nitro groups or $R_8$ and $R_9$ together with a portion of the naphthalene ring form a 5-member carbon ring and $R_{15}$ is an optionally substituted organic group bonded to the boron through a C-B bond.

2. The protected boronic acid of claim 1 wherein $R_2$ and $R_3$ are methyl groups, $R_4$ and $R_5$ are both hydrogens, and $R_6$ and $R_7$ are hydrogen or halogens.

3. The protected boronic acid of claim 1 wherein $R_8$ and $R_9$ are hydrogens.

4. The protected boronic acid of claim 1 wherein $R_{15}$ is an optionally substituted alkyl, alkenyl, alkynyl, aryl, heteroaryl, heterocyclyl, or carbocyclyl group.

5. The protected boronic acid of claim 1 wherein $R_{15}$ is an optionally substituted alkyl, alkenyl, alkynyl, cycloalkyl, cycloalkenyl or aryl.

6. The protected boronic acid claim 1 wherein $R_{15}$ is an optionally substituted aryl, heteroaryl, or heterocyclyl group.

7. The protected boronic acid of claim 1 wherein $R_{15}$ is an organic group contains one or more metals.

8. The protected boronic acid of claim 1 wherein substitution, if present, is substitution with one or more oxo group, thioxo group, halogen, nitro, cyano, cyanate, azido, thiocyano, isocyano, isothiocyano, sulfhydryl, hydroxyl, alkyl, alkoxy, alkenyl, alkenyloxy, alkynyl, alkynyloxy, aryl, aryloxy, heteroaryl, heteroaryloxy, carbocyclyl, carbocyclyloxy, heterocyclyl, heterocyclyloxy, alkylthio, alkenylthio, alkynylthio, arylthio, thioheteroaryl, thioheteroaryl, thiocarbocyclyl, thioheterocyclyl, —CO—R, —COH, —O—CO—R, —O—CO—H, —CO—O—R, —CO—OH, —CO—O—CO—R, —CO—N(R)$_2$, —CO—NHR, —CO—NH$_2$, —NR—CO—R, —NH—CO—R, —NHR, —N(R)$_2$, —O—SO$_2$—R, —SO$_2$—R, —SO$_2$—NHR, —SO$_2$—N(R)$_2$, —NR—SO$_2$—R, —NH—SO$_2$—R, —NR—CO—N(R)$_2$, —NH—CO—NHR, —O—PO(OR)$_2$, —O—PO(OR)(N(R)$_2$), —O—PO(N(R)$_2$)$_2$, —N—PO(OR)$_2$, —N—PO(OR)(N(R)$_2$), —P(R)$_2$, —B(OH)$_2$, —B(OH)(OR), —B(OR)$_2$, —O—Si(R)$_3$, or —SeR, where each R independently is an organic group or two R within the same substituent can together form a carbocyclic or heterocyclic ring having 3 to 10 ring atoms.

9. A protected benzoxaborole or benzoxaborin of formula:

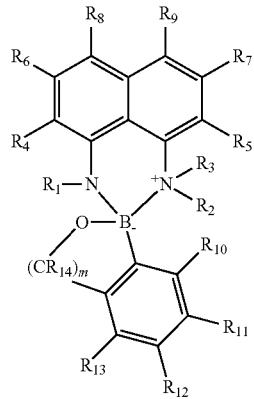

where:
$R_1$ is a methyl or ethyl group;
$R_2$ and $R_3$ are independently methyl or ethyl groups;
$R_4$ and $R_5$ are independently halogens or hydrogens;
$R_6$ and $R_7$ are independently hydrogens, halogens, or nitro groups; and
$R_8$ and $R_9$ are independently hydrogens, halogens or nitro groups or $R_8$ and $R_9$ together with a portion of the naphthalene ring form a 5-member carbon ring
m is 1 or 2; and
$R_{10}$-$R_{13}$ and each $R_{14}$ is independently hydrogen, a non-hydrogen substituent or an organic group.

10. The protected boronic acid of claim 9 where $R_1$-$R_3$ are all methyl groups.

11. The protected boronic acid of claim 9 where all of $R_4$-$R_7$ are hydrogens or halogens.

12. The protected boronic acid of claim 9 wherein $R_8$ and $R_9$ are hydrogens.

13. The protected boronic acid of claim 9 where all $R_{14}$ are hydrogens or alkyl groups having 1-3 carbon atoms.

14. The protected boronic acid of claim 9 where the organic group is an optionally substituted alkyl, alkenyl, alkynyl, aryl, heteroaryl, heterocyclyl, or carbocyclyl group.

15. The protected boronic acid of claim 9 where the organic group is an optionally substituted alkyl, alkenyl, alkynyl, cycloalkyl, cycloalkenyl or aryl.

16. The protected boronic acid of claim 9 where the organic group is an optionally substituted aryl, heteroaryl, or heterocyclyl group.

17. The protected boronic acid of claim 9 wherein the non-hydrogen substituent substitution is halogen, nitro, cyano, cyanate, azido, thiocyano, isocyano, isothiocyano, sulfhydryl, hydroxyl, alkyl, alkoxy, alkenyl, alkenyloxy, alkynyl, alkynyloxy, aryl, aryloxy, heteroaryl, heteroaryloxy, carbocyclyl, carbocyclyloxy, heterocyclyl, heterocyclyloxy, alkylthio, alkenylthio, alkynylthio, arylthio, thioheteroaryl, thioheteroaryl, thiocarbocyclyl, thioheterocyclyl, —COR, —COH, —O—CO—R, —OC—OH, —CO—OR, —CO—OH, —CO—O—CO—R, —CON(R)$_2$, —CO—NHR, —CO—NH$_2$, —NR—CO—R, —NH—CO—R, —NHR, —N(R)$_2$, —O—SO$_2$—R, —SO$_2$—R, —SO$_2$—NHR, —SO$_2$—N(R)$_2$, —NR—SO$_2$—R, —NH—SO$_2$—R, —NRCO—N(R)$_2$, —NH—CO—NHR, —O—PO(OR)$_2$, —O—PO(OR)(N(R)$_2$), —O—PO(N(R)$_2$)$_2$, —N—PO(OR)$_2$, —N—PO(OR)(N(R)$_2$), —P(R)$_2$, —B(OH)$_2$, —B(OH)(OR), —B(OR)$_2$, —O—Si(R)$_3$, or —SeR, where each R independently is an organic group or two R within the same substituent optionally together form a carbocyclic or heterocyclic ring having 3 to 10 ring atoms.

18. The protected boronic acid of claim 9 wherein $R_{10}$ to $R_{13}$ are selected from hydrogen or a non-hydrogen substituent.

19. A method for conducting a reaction employing one or more protected organoboronic acids of claim 1.

20. A method for conducting a reaction employing one or more protected benzoxaboroles or benzoxaborins of claim 9.

21. The protected boronic acid of claim 8 where each R independently is an alkyl, alkenyl, alkynyl, aryl, heteroaryl, carbocyclyl, or heterocyclyl group.

22. The protected boronic acid of claim 17 where each R independently is an alkyl, alkenyl, alkynyl, aryl, heteroaryl, carbocyclyl, or heterocyclyl group.

23. The method of claim 19 which comprises preparing the one or more protected organoboronic acids by reaction of the one or more unprotected organoboronic acids with a protecting group precursor of formula:

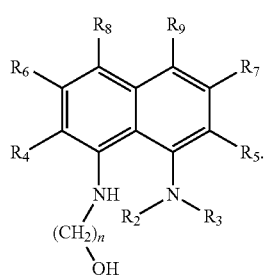

24. The method of claim 23 wherein the protecting group precursor is that of formula:

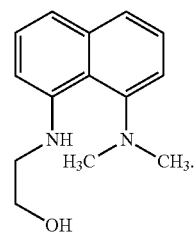 [SMILES: CN(C)c1cccc2cccc(NCCO)c12]

25. The method of claim 20 which comprises preparing the one or more protected benzoxaboroles or protected benzoxaborins by reaction of the one or more unprotected benzoxaboroles or unprotected benzoxaborins with a protecting group precursor of formula:

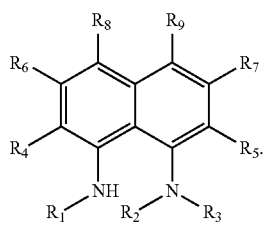

26. The method of claim 25 wherein the protecting group precursor is 1-di methylamino-8-methylaminonaphthalene.

27. A method for preparing a protected organoboronic acid of claim 1 which comprises reacting the unprotected organoboronic acid with a protecting group precursor of formula:

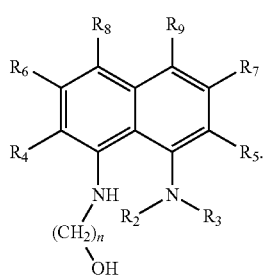

28. The method of claim 27 wherein the protecting group precursor is

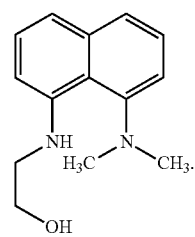

29. A method for preparing a protected benzoxaborole or protected benzoxaborin of claim 9 which comprises reacting the unprotected benzoxaborole or benzoxaborin with a protecting group precursor of formula:

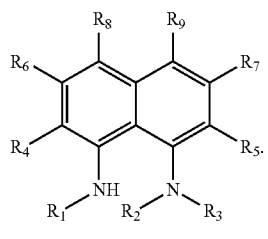
30. The method of claim 29 wherein the protecting group precursor is 1-dimethylamino-8-methylaminonaphthalene.
* * * * *

UNITED STATES PATENT AND TRADEMARK OFFICE
CERTIFICATE OF CORRECTION

PATENT NO. : 9,085,590 B2
APPLICATION NO. : 14/213433
DATED : July 21, 2015
INVENTOR(S) : Raines It is certified that error appears in the above-identified patent and that said Letters Patent is hereby corrected as shown below:

In the claims

Claim 6, column 32, line 4, replace "claim 1" with --of claim 1--

Claim 8, column 32, line 16, delete redundant "thioheteroaryl"

Claim 9, column 32, line 55, replace "groups; and" with --groups;--

Claim 9, column 32, line 58," replace "5-member carbon ring" with --5-member carbon ring;--

Claim 17, column 33, line 21, delete "thioheteroaryl"

Signed and Sealed this
First Day of March, 2016

Michelle K. Lee
*Director of the United States Patent and Trademark Office*